United States Patent
Jaume et al.

(10) Patent No.: US 12,161,704 B2
(45) Date of Patent: *Dec. 10, 2024

(54) IMMUNOSUPPRESSIVE ANTIGEN-SPECIFIC CHIMERIC ANTIGEN RECEPTOR TREG CELLS FOR PREVENTION AND/OR TREATMENT OF AUTOIMMUNE AND ALLOIMMUNE DISORDERS

(71) Applicant: The University of Toledo, Toledo, OH (US)

(72) Inventors: Juan C. Jaume, Toledo, OH (US); Shahnawaz Imam, Toledo, OH (US)

(73) Assignee: The University of Toledo, Toledo, OH (US)

( * ) Notice: Subject to any disclaimer, the term of this patent is extended or adjusted under 35 U.S.C. 154(b) by 408 days.

This patent is subject to a terminal disclaimer.

(21) Appl. No.: 17/291,853

(22) PCT Filed: Nov. 8, 2019

(86) PCT No.: PCT/US2019/060593
§ 371 (c)(1),
(2) Date: May 6, 2021

(87) PCT Pub. No.: WO2020/097543
PCT Pub. Date: May 14, 2020

(65) Prior Publication Data
US 2022/0008522 A1    Jan. 13, 2022

Related U.S. Application Data

(60) Provisional application No. 62/757,313, filed on Nov. 8, 2018.

(51) Int. Cl.
| | | |
|---|---|---|
| *A61K 39/00* | (2006.01) | |
| *A61P 3/10* | (2006.01) | |
| *C07K 14/705* | (2006.01) | |
| *C07K 14/725* | (2006.01) | |
| *C07K 16/40* | (2006.01) | |
| *C12N 5/0783* | (2010.01) | |

(52) U.S. Cl.
CPC ...... *A61K 39/0008* (2013.01); *A61K 39/4611* (2023.05); *A61K 39/4621* (2023.05); *A61K 39/4631* (2023.05); *A61K 39/46433* (2023.05); *A61K 39/46434* (2023.05); *A61P 3/10* (2018.01); *C07K 14/7051* (2013.01); *C07K 14/70521* (2013.01); *C07K 16/40* (2013.01); *C12N 5/0636* (2013.01); *C12N 5/0637* (2013.01); *A61K 2239/31* (2023.05); *C07K 2319/03* (2013.01); *C07K 2319/33* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 2016/0022788 A1 | 1/2016 | Avram | |
| 2017/0274095 A1 | 9/2017 | Meyer et al. | |
| 2019/0031759 A1* | 1/2019 | Reiter | ................ C07K 16/2833 |

FOREIGN PATENT DOCUMENTS

| | | |
|---|---|---|
| WO | 2016174652 A1 | 11/2016 |
| WO | 2017100428 A1 | 6/2017 |

OTHER PUBLICATIONS

Gacerez AT, Arellano B, Sentman CL. How Chimeric Antigen Receptor Design Affects Adoptive T Cell Therapy. J Cell Physiol. Dec. 2016;231(12):2590-8. doi: 10.1002/jcp.25419. Epub Jun. 2, 2016. PMID: 27163336; PMCID: PMC4993661. (Year: 2016).*
Sayour EJ, Mitchell DA. Immunotherapy for Pediatric Brain Tumors. Brain Sci. Oct. 21, 2017;7(10):137. doi: 10.3390/brainsci7100137. PMID: 29065490; PMCID: PMC5664064. (Year: 2017).*
Del Baldo G, et al. The peculiar challenge of bringing CAR-T cells into the brain: Perspectives in the clinical application to the treatment of pediatric central nervous system tumors. Front Immunol. Mar. 21, 2023;14:1142597. doi: 10.3389/fimmu.2023.1142597. PMID: 37025994; PMCID: PMC10072260. (Year: 2023).*
The Extended European Search Report, Application No. 19882569. 7, dated Jan. 26, 2023.
International Search Report and Written Opinion, Application No. PCT/US2019/060593, dated Mar. 19, 2020.
The Partial Supplementary European Search Report, Application No. 19882569.7, dated Oct. 20, 2022.

* cited by examiner

*Primary Examiner* — Allison M Fox
*Assistant Examiner* — Alyssa G Weston
(74) *Attorney, Agent, or Firm* — MacMillan, Sobanski & Todd, LLC

(57) ABSTRACT

Described herein are immunoresponsive cells which are useful for their preventive and therapeutic potential against autoimmune diseases and rejections of solid organ transplants.

14 Claims, 19 Drawing Sheets
(18 of 19 Drawing Sheet(s) Filed in Color)
Specification includes a Sequence Listing.

| Proliferation / Replication index of CAR-Treg (CD25+) and Tresp (CD4+ + CD25-) (n=3-4) | | | | | |
|---|---|---|---|---|---|
| | Tresp:Treg (8:1) | Tresp:Treg (4:1) | Tresp:Treg (2:1) | Tresp:Treg (1:1) | Tresp:Treg (0:1) |
| CD25/Proliferation Index (Mean ± SE) | 2.48 ± 0.14 | 2.13 ± 0.11 | 2.25 ± 0.49 | 2.23 ± 0.36 | 2.45 ± 0.20 |
| Tresp/Proliferation Index (Mean ± SE) | 1.54 ± 0.20 | 1.67 ± 0.35 | 1.20 ± 0.02 | 1.71 ± 0.33 | 0.00 |
| CD25/Replication Index (Mean ± SE) | 8.57 ± 2.02 | 5.60 ± 0.79 | 6.21 ± 2.07 | 8.20 ± 3.37 | 5.99 ± 0.69 |
| Tresp/Replication Index (Mean ± SE) | 3.34 ± 0.56 | 3.70 ± 1.04 | 2.47 ± 0.06 | 3.86 ± 1.03 | 0.00 |

FIG. 7E

IMMUNOSUPPRESSIVE ANTIGEN-SPECIFIC CHIMERIC ANTIGEN RECEPTOR TREG CELLS FOR PREVENTION AND/OR TREATMENT OF AUTOIMMUNE AND ALLOIMMUNE DISORDERS

CROSS-REFERENCE TO RELATED APPLICATIONS

This is the national phase entry of international application PCT/US2019/060593, filed under the authority of the Patent Cooperation Treaty on Nov. 8, 2019, published; which claims priority to U.S. Provisional Application No. 62/757,313, filed under 35 U.S.C. § 111 (b) on Nov. 8, 2018. The entire disclosure of each of the aforementioned applications is expressly incorporated herein by reference for all purposes.

STATEMENT REGARDING FEDERALLY SPONSORED RESEARCH

The invention was not made with any U.S. Government support, and the United States Government has no rights in the invention.

SEQUENCE LISTING

The instant application contains a Sequence Listing which has been submitted electronically in ASCII format and is hereby incorporated by reference in its entirety. The ASCII copy, created on Nov. 7, 2019, is named 420_60439_SEQ_LIST_D2019-07.txt and is 4,245 bytes in size.

BACKGROUND OF THE INVENTION

Autoimmune disorders are caused by dysfunctional immune responses directed against the body's own tissues, resulting in chronic, multisystem impairments that differ in clinical manifestations, course, and outcome.

The therapeutic application of regulatory T cells (Tregs) for the treatment of autoimmune diseases is limited by the scarcity of antigen-specific Tregs.

One approach to endow effector T cells with a desired antigen specificity uses chimeric T cell antigen receptors with antibody-type specificity. Cellular therapies with antibody-type specific chimeric antigen receptor (CAR)-redirected cytotoxic T cells have shown efficacy in the treatment of hematologic malignancies.

Accordingly, employing such chimeric immune receptors to redirect Tregs to sites of autoimmune attack would be a useful therapeutic approach to alleviate a broad scope of diseases in which an uncontrolled autoimmune response plays a major role.

If antigen-specific Tregs could be produced on demand against a desire autoimmune target, antigen-specific immune suppression of autoimmune diseases would be achievable.

As such, there is an urgent need for compositions and approaches to treating immune-related disorders or deficient T-cell tolerance mediated immune disorders.

SUMMARY OF THE INVENTION

The present invention relates to reagents, compositions and methods for modulating the activation of T cells, and for modulating immune responses, including but not limited to type 1 diabetes (T1D), autoimmune tolerance and transplantation tolerance.

In general, described herein is the development of pancreatic beta cell-specific CAR-Tregs with preventive and therapeutic capacity against T1D.

The present disclosure describes using CAR technology to generate potent, functional, and stable, GAD65 antigen-specific CAR-Tregs that can prevent the development of autoimmune diabetes or T1D.

Also described herein is the antigen-specific CAR-Treg development for prevention and treatment of other autoimmune diseases and rejections of solid organ transplants.

In a specific embodiment, the subject is afflicted with an autoimmune disease, with host versus graft disease (HVGD), or the subject is an organ transplant recipient.

In a first aspect, provided herein is an immunoresponsive cell having a chimeric antigen receptor (CAR) that binds to glutamic acid decarboxylase 65 kDA (GAD65) in the cell.

The CAR comprises: a) an intracellular signaling domain of a CD3ξ polypeptide and an intracellular signaling domain of CD28 hinge-transmembrane-intracellular region, and b) an extracellular polypeptide recognizing: at least a part of an amino acid sequence selected from the amino acids having SEQ ID Nos: 1-6; or, at least one complete amino acid sequence selected the amino acids having SEQ ID Nos: 1-6

In certain embodiments, the immunoresponsive cell is selected from the group consisting of: T cells, cytotoxic T cells, regulatory T cells, and combinations thereof.

In certain embodiments, the cell comprises a pancreatic beta cell-specific chimeric antigen receptor (CAR) regulatory T cell (Treg) that expresses at least one extracellular polypeptide and is capable of affecting Teff cells.

In certain embodiments, the extracellular polypeptide is a GAD65 MAb antigen binding domain which recognizes at least a part of an amino acid sequence selected from the amino acids having SEQ ID Nos: 1-6; or, at least one complete amino acid sequence selected the amino acids having SEQ ID Nos: 1-6.

In another aspect, provided herein is a pharmaceutical composition comprising an effective amount of an immunoresponsive cell described herein and a pharmaceutically acceptable excipient.

In another aspect, provided herein is a kit for the prevention or therapeutic treatment of Type 1 diabetes (T1D), comprising: a) the pharmaceutical composition described herein; and, b) instructions for use in the therapeutic treatment of T1D.

In another aspect, provided herein is a method of lengthening survival of a subject having type 1 diabetes (T1D), the method comprising: administering, to the subject, an effective amount of an immunoresponsive cell described herein, thereby lengthening survival of the subject.

In another aspect, provided herein is a method of preventing or treating type 1 diabetes (T1D), the method comprising: administering, to the subject, an effective amount of an immunoresponsive cell described herein, thereby treating or preventing the T1D in the subject.

In certain embodiments, the subject is a human.

In another aspect, provided herein is an immunoresponsive cell for treating an autoimmune endocrinopathy having a chimeric antigen receptor (CAR) that binds to at least one antigen. The CAR includes: a) an intracellular signaling domain, and b) an extracellular polypeptide comprising an antigen binding region MAb which recognizes an amino acid sequence of the at least one antigen. The autoimmune endocrinopathy and the antigen can be selected as described herein.

In another aspect, provided herein is a method of treating or preventing an autoimmune endocrinopathy in a subject, the method comprising: administering, to the subject, an effective amount of the immunoresponsive cell, thereby treating or preventing the autoimmune endocrinopathy in the subject.

In another aspect, provided herein is a method of lengthening survival of a subject having an autoimmune endocrinopathy, the method comprising: administering, to the subject, an effective amount of the immunoresponsive cell, thereby lengthening survival of the subject.

In another aspect, provided herein is an immunoresponsive cell for treating an organ-specific autoimmune disease having a chimeric antigen receptor (CAR) that binds to at least one antigen. The CAR includes: a) an intracellular signaling domain, and b) an extracellular polypeptide comprising an antigen binding region MAb which recognizes an amino acid sequence of the at least one antigen. The organ-specific autoimmune disease and the antigen can be selected as described herein.

In another aspect, provided herein is a method of treating or preventing an organ-specific autoimmune disease in a subject, the method comprising: administering, to the subject, an effective amount of the immunoresponsive cell, thereby treating or preventing the organ-specific autoimmune disease in the subject.

In another aspect, provided herein is a method of lengthening survival of a subject having an organ-specific autoimmune disease, the method comprising: administering, to the subject, an effective amount of the immunoresponsive cell, thereby lengthening survival of the subject.

In another aspect, provided herein is an immunoresponsive cell for treating an alloimmune transplant intolerance having a chimeric antigen receptor (CAR) that binds to at least one antigen. The CAR includes: a) an intracellular signaling domain, and b) an extracellular polypeptide comprising an antigen binding region MAb which recognizes an amino acid sequence of the at least one antigen. The alloimmune transplant and the antigen can be selected as described herein.

In another aspect, provided herein is a method of treating or preventing an alloimmune transplant intolerance in a subject, the method comprising: administering, to the subject, an effective amount of the immunoresponsive cell, thereby treating or preventing the alloimmune transplant intolerance in the subject.

In another aspect, provided herein is a method of lengthening survival of a subject having an alloimmune transplant intolerance the method comprising: administering, to the subject, an effective amount of the immunoresponsive cell, thereby lengthening survival of the subject.

In certain embodiments, the MAb variable region of the CAR enhances an immune response in a subject by binding specific antigens in a target cell.

In certain embodiments, the target cell is a cell in a subject that is affected by the autoimmune endocrinopathy, the organ-specific autoimmune disease, or the alloimmune transplant intolerance.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the Patent Office upon request and payment of the necessary fee.

FIG. 7A=Tresp. (CD4+CD25); FIG. 7B=CAR-Treg (CD25+).

FIG. 7E: Table of summarized data of in vitro suppression assay at different ratios of Tresp and CAR-Treg, and their proliferative/replicative index FIGS. 7C-7D.

DETAILED DESCRIPTION

Figure 1A:
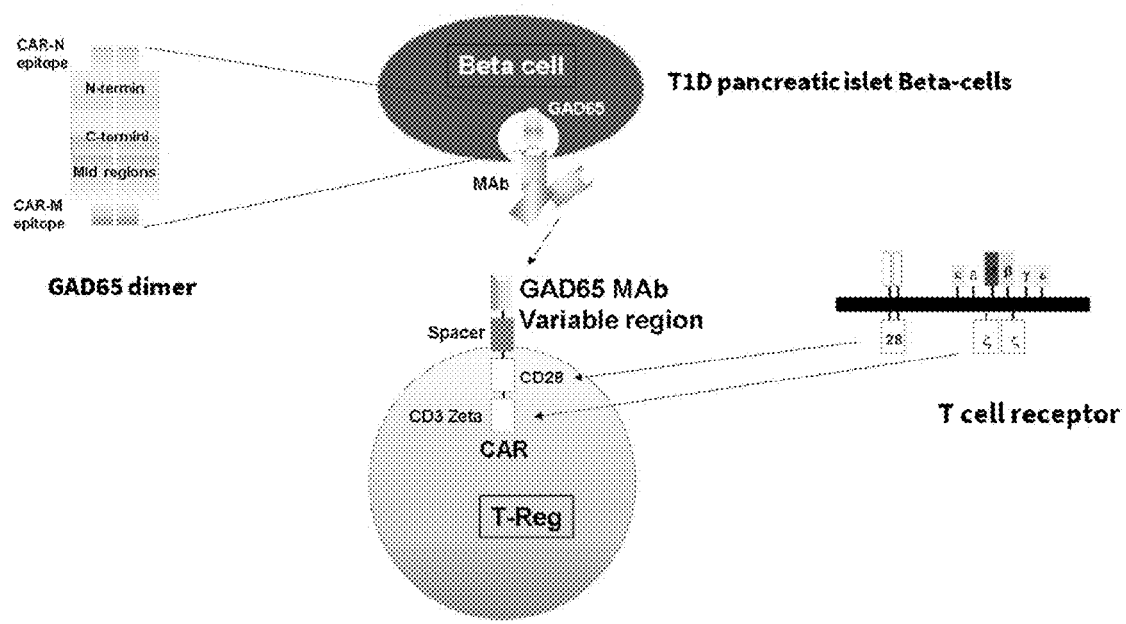
FIG. 1A: CAR-Treg design scheme.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

General methods in molecular and cellular biochemistry can be found in such standard textbooks as Molecular Cloning: A Laboratory Manual, 3rd Ed. (Sambrook et al., CSH Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors.

Definitions

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about." The term "about" with respect to numerical values means within 5%.

As used herein, the term "administering," or "administration" refer to the placement of an agent into a subject by a method or route which results in at least partial localization of such agents at a desired site, such as a site of inflammation or tumor, such that a desired effect(s) is produced.

As used herein, "modulating" or "modulate" generally means either reducing or inhibiting the expression and/or activity of, or alternatively increasing the expression and/or activity of, a target molecule, e.g., as measured using a suitable in vitro, cellular, or in vivo assay. In particular, "modulating" or "modulate" can mean either reducing or inhibiting the expression and/or activity of, or alternatively increasing a (relevant or intended) biological activity and/or expression of, a target molecule, as measured using a suitable in vitro, cellular or in vivo assay (which will usually depend on the target involved), by at least 5%, at least 10%, at least 25%, at least 50%, at least 60%, at least 70%, at least 80%, at least 90%, or more, inclusive, compared to activity of the target in the same assay under the same conditions but without the presence of an agent. Thus, as used herein, the term "modulating" can refer to an increase or decrease in the expression and/or activity relative to a subject not treated with an agent that modulates the expression and/or activity. An "increase" or "decrease" refers to a statistically significant increase or decrease respectively. For the avoidance of doubt, an increase or decrease will be at least 10% relative to a reference, such as at least 10%, at least 20%, at least 30%, at least 40%, at least 50%, at least 60%, at least 70%, at least 80%, at least 90%, at least 95%, at least 97%, at least 98%, or more, up to and including at least 100% or more, inclusive, in the case of an increase, for example, at least 2-fold, at least 3-fold, at least 4-fold, at least 5-fold, at least 6-fold, at least 7-fold, at least 8-fold, at least 9-fold, at least 10-fold, at least 50-fold, at least 100-fold, or more.

The term "composition" as used herein is intended to encompass a product comprising the specified ingredients in the specified amounts, as well as any product that results, directly or indirectly, from combinations of the specified ingredients in the specified amounts.

By "comprising" it is meant that the recited elements are required in the composition/method/kit, but other elements may be included to form the composition/method/kit etc. within the scope of the claim.

By "consisting essentially of", it is meant a limitation of the scope of composition or method described to the specified materials or steps that do not materially affect the basic and novel characteristic(s) of the subject invention.

By "consisting of", it is meant the exclusion from the composition, method, or kit of any element, step, or ingredient not specified in the claim.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy may be administered during the symptomatic stage of the disease, and in some cases after the symptomatic stage of the disease.

A "therapeutically effective amount" is intended for an amount of active agent which is necessary to impart therapeutic benefit to a subject. For example, a "therapeutically effective amount" is an amount which induces, ameliorates or otherwise causes an improvement in the pathological symptoms, disease progression or physiological conditions associated with a disease or which improves resistance to a disorder.

The term "genetic modification" means any process that adds, deletes, alters, or disrupts an endogenous nucleotide sequence and includes, but is not limited to viral mediated gene transfer, liposome mediated transfer, CRISPER CAS9 mediated gene transformation, transfection and transduction.

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments $F(ab')_2$, and Fab. $F(ab')_2$, and Fab fragments that lack the Fe fragment of intact antibody, clear more rapidly from the circulation, and may have less non-specific tissue binding of an intact antibody. The antibodies can whole native antibodies, bispecific antibodies; chimeric antibodies; Fab, Fab', single chain V region fragments (scFv), fusion polypeptides, and unconventional antibodies.

The term "antigen recognizing receptor" as used herein refers to a receptor that is capable of activating an immune cell (e.g., a T-cell) in response to antigen binding. Exemplary antigen recognizing receptors may be native or endogenous T cell receptors or chimeric antigen receptors in which an antigen-binding domain is fused to an intracellular signaling domain capable of activating an immune cell (e.g., a T-cell).

The term "chimeric antigen receptor" or "CAR" as used herein refers to an antigen-binding domain that is fused to an intracellular signaling domain capable of activating or stimulating an immune cell. Most commonly, the CAR's extracellular binding domain is composed of a single chain variable fragment (scFv) derived from fusing the variable heavy and light regions of a murine or humanized monoclonal antibody. Alternatively, scFvs may be used that are derived from Fab's (instead of from an antibody, e.g., obtained from Fab libraries). In various embodiments, this scFv is fused to a transmembrane domain and then to an intracellular signaling domain. "First-generation" CARs include those that solely provide CD3ξ signals upon antigen binding, "Second-generation" CARs include those that provide both costimulation (e.g. CD28 or CD137) and activation (CD3ξ). "Third-generation" CARs include those that provide multiple costimulation (e.g. CD28 and CD137) and activation (CD3). In various embodiments, the CAR is selected to have high affinity or avidity for the antigen.

As used herein, the term "single-chain variable fragment" or "scFv" is a fusion protein of the variable regions of the heavy (VH) and light chains (VL) of an immunoglobulin covalently linked to form a VH::VL heterodimer. The heavy (VH) and light chains (VL) are either joined directly or joined by a peptide-encoding linker (e.g., 10, 15, 20, 25 amino acids), which connects the N-terminus of the VH with the C-terminus of the VL, or the C-terminus of the VH with the N-terminus of the VL. The linker/spacer can be in glycine for flexibility, as well as serine or threonine for solubility. Despite removal of the constant regions and the introduction of a linker, scFv proteins retain the specificity of the original immunoglobulin.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

By "exogenous" is meant a nucleic acid molecule or polypeptide that is not endogenously present in the cell, or not present at a level sufficient to achieve the functional effects obtained when over-expressed. The term "exogenous" would therefore encompass any recombinant nucleic acid molecule or polypeptide expressed in a cell, such as foreign, heterologous, and over-expressed nucleic acid molecules and polypeptides.

By a "heterologous nucleic acid molecule or polypeptide" is meant a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

By "immunoresponsive cell" is meant a cell that functions in an immune response or a progenitor, or progeny thereof.

By "increase" is meant to alter positively by at least 5%. An alteration may be by 5%, 10%, 25%, 30%, 50%, 75%, or even by 100%.

By "isolated cell" is meant a cell that is separated from the molecular and/or cellular components that naturally accompany the cell.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials like endotoxin free such that any impurities do not materially affect the biological properties of the protein or cause other adverse consequences. That is, a nucleic acid or peptide is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

"Linker" or "spacer", as used herein, shall mean a functional group (e.g., chemical or polypeptide) that covalently attaches two or more polypeptides or nucleic acids so that they are connected to one another. As used herein, a "peptide linker" refers to one or more amino acids used to couple two proteins together (e.g., to couple VH and VL domains).

"Variant" refers to polypeptides having amino acid sequences that differ to some extent from a native sequence polypeptide. Ordinarily, amino acid sequence variants will possess at least about 80% sequence identity, more preferably, at least about 90% homologous by sequence. The amino acid sequence variants may possess substitutions, deletions, and/or insertions at certain positions within the reference amino acid sequence.

A "variant" of a protein of interest, as used herein, refers to an amino acid sequence that is altered by one or more amino acids. The variant may have "conservative" changes, wherein a substituted amino acid has similar structural or chemical properties, (e.g., replacement of leucine with isoleucine). More rarely, a variant may have "nonconservative" changes (e.g., replacement of a glycine with a tryptophan). Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

As used herein, the term "graft" refers to organs and/or tissues which can be obtained from a first mammal (or donor) and transplanted into a second mammal (a recipient), preferably a human. The term "graft" encompasses, for example, skin, organs such as heart, lung, heart-lung (e.g., heart and a single lung, heart and both lungs), liver, kidney, pancreas (e.g., islet cells, P-cells), parathyroid, bowel (e.g., colon, small intestine, duodenum). A graft can be obtained from a suitable mammal (e.g., human, pig, baboon, chimpanzee), or under certain circumstances a graft can be produced in vitro by culturing cells which were obtained from a suitable mammal. A graft is preferably obtained from a human.

As used herein, the term "subject" denotes a mammal, such as canines; felines; equines; bovines; ovines; etc. and primates, particularly humans. Animal models, particularly small mammals, e.g. murine, etc. can be used for experimental investigations. Preferably a subject is a human.

"Non-immunogenic" refers to a material that does not initiate, provoke or enhance an immune response where the immune response includes the adaptive and/or innate immune responses.

The term "gene" means the segment of DNA involved in producing a polypeptide chain; it includes regions preceding and following the coding region "leader and trailer" as well as intervening sequences (introns) between individual coding segments (exons). Some genes may be developed which lack, in whole or in part, introns. Some leader sequences may enhance translation of the nucleic acid into polypeptides.

The term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The terms "polypeptide" and "protein" are used interchangeably herein. The term "preventing" is art-recognized, and when used in relation to a condition, is well understood in the art, and includes administering, prior to onset of the condition, a composition that reduces the frequency of, reduces the severity of, or delays the onset of symptoms of a medical condition in a subject relative to a subject which does not receive the composition.

As used herein, "type 1 diabetes" comprises one or more of type 1 diabetes, insulin-dependent diabetes mellitus, idiopathic diabetes, juvenile type 1 diabetes, latent autoimmune diabetes in adults. Conditions relating to type 1 diabetes include, neuropathy including polyneuropathy, mononeuropathy, peripheral neuropathy and autonomicneuropathy; eye complications: glaucoma, cataracts, and/or retinopathy; kidney complications: diabetic nephropathy.

Prevention of an infection includes, for example, reducing the number of diagnoses of the infection in a treated population versus an untreated/control population, and/or delaying the onset of symptoms of the infection in a treated population versus an untreated control population.

General Description

In general, the immunoresponsive cell includes a chimeric antigen receptor (CAR) having extracellular polypeptide that recognizes an epitope of a recognition domain. The extracellular polypeptide is a MAb (monoclonal antibody) Variable region.

In one embodiment, the extracellular peptide GAD65 MAb is the part of the CAR that recognizes at least a part of an amino acid sequence (epitope) of one of SEQ ID Nos: 1-6. The term "extracellular" is used herein to differentiate from intracellular (CD3ξ and CD28, as shown in FIG. 1A). In this CAR, the GAD65 MAb Variable region is the extracellular recombinant polypeptide expressed by the immunoresponsive (Treg) cells.

For example, the extracellular polypeptide (GAD65 MAb Variable region of CAR) is a GAD65 antigen binding domain which recognizes at least a part of one amino acid sequence selected from one of SEQ ID NOs: 1-6.

The MAb Variable region of any CAR (including GAD65 CAR) of immunoresponsive cells will be activated (enhanced immune response) by binding specific antigens (either GAD65 or any of the desired antigens for other autoimmune diseases and solid organ transplant rejection)

Thus, in one embodiment, the GAD65 CAR-Treg cell is basically made of a Treg cell (for example, isolated from the peripheral blood of the subject) and a construct (CAR) that recognizes a specific antigen via a MAb variable region.

The CAR components (expressed by CAR-Treg cells), as shown in FIG. 1A include intracellular (CD3ξ and CD28), spacer and extracellular (MAb variable region). The expression of the CAR follows the pathway of expression of any cellular protein (DNA→RNA→Protein). The different components (polypeptides CD3ξ, CD8, spacer and MAb variable region) are linked together by peptide bonds.

For example, the MAb variable regions that recognize GAD65 epitopes (for which humans with T1D make antibodies against) are assembled together with the other components (CD3ξ, CD8, spacer).

In other examples, selected autoantigens are sued to create CAR-Tregs to treat autoimmune diseases and solid organ transplant rejection. Non-limiting examples of such antigens (for which humans make antibodies against) are listed in Tables 1-3 below. The epitopes of those antigens are selected (as like in GAD65) in order to create epitope-specific CAR-Tregs.

According to at least some embodiments, there is provided a use of an isolated soluble paratope polypeptide, or fragment or variant or homolog or a fusion protein or conjugate containing same, or a polypeptide comprising the extracellular domain of any one of amino acids binding SEQ ID NOs 1-6, or fragments or variants or homologs thereof or a fusion protein or conjugate containing same, or a pharmaceutical composition containing any of the foregoing, adapted for treatment of immune related disorder including T1D.

Optionally the paratope polypeptidecomprises a sequence of amino acid residues having at least 95% sequence identity with amino acid residues depicted in any of SEQ ID NOs: 1-6, or a fragment, or a variant, or a homolog thereof, adapted for treatment. Optionally the polypeptide is attached to a detectable or therapeutic moiety.

According to at least some embodiments, there is provided a method for preventing and/or treating immune related disorder, where the treatment does not cause a global immunosuppression of the immune system in the subject, comprising administering to a subject in need thereof a pharmaceutical composition comprising a paratope polypeptide binding amino acid residues depicted in any of SEQ ID NOs 1-6, or a fragment or a variant or a homolog thereof, optionally provided as a pharmaceutical composition thereof.

Optionally treating comprises one or more of curing, managing, reversing, attenuating, alleviating, minimizing, suppressing, managing, or halting the deleterious effects of the above-described diseases.

General Methods

In general, the Tregs that have been modified with the desired construct(s) are grown in culture under selective conditions and cells that are selected as having the construct may be expanded and further analyzed, using, for example; the polymerase chain reaction/western blot for determining the presence of the construct in the host cells. Once the modified host cells have been identified, they may then be used as planned, e.g., expanded in culture or introduced into a host organism.

Depending upon the nature of the cells, the cells may be introduced into a host organism, e.g. a mammal, including humans, in a wide variety of ways. For example, the cells may be introduced at the site of the inflammatory lesion.

EXAMPLES

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

More specifically, various aspects of the present embodiments provide for methods and compositions for treatment of immune-related diseases or disorders and/or therapy monitoring.

In some embodiments, the methods and compositions described herein are directed to treatment and/or therapy monitoring of Type 1 diabetes (T1D).

In other embodiments, the methods and compositions described herein are directed to treatment and/or therapy monitoring of autoimmune diseases and/or transplant rejections.

In one specific embodiment, the subject is a recipient of an allogenic transplant. The transplant can be any organ or tissue transplant, including but not limited to pancreas, kidney, heart, lung, liver, intestine, bone, cartilage or skin. Transplantation tolerance, as used herein, refers to a lack of rejection of the donor organ by the recipient's immune system. Furthermore, the agents can be used for preventing or reducing the likelihood of being afflicted with rejection of tissue or cell transplants.

Table 1 below provides non-limiting examples useful antigens for specific autoimmune endocrinopathy.

TABLE 1

| AUTOIMMUNE ENDOCRINOPATHY | ANTIGEN |
|---|---|
| Diabetes | GAD65 |
| | Insulinoma Associated protein 2 (IA-2) |
| Thyroid autoimmune diseases (Hashimoto's and Graves') | Thyroid Peroxidase (TPO) |
| | Thyrotropin Receptor (TSHR) |
| Adrenal (autoimmune) insufficiency (Addison's) | Adrenocorticotropic Hormone Receptor (ACTHR), 21-hydroxylase |
| Oophoritis (Premature ovarian failure) | 17-alpha-hydroxylase |
| | P450 side-chain cleavage enzyme |
| Orchitis | Sperm (various epitopes of Anti-Sperm-Antibodies) |
| Lymphocytic hypophysitis | Pituitary cytosolic protein. |
| Autoimmune hypoparathyroidism | Calcium Sensing Receptor (CaSR) |
| | NACHT, LRR and PYD domains-containing protein 5 (NALP5) |

Table 2 below provides non-limiting examples useful antigens for various organ-specific autoimmune diseases.

TABLE 2

| ORGAN-SPECIFIC AUTOIMMUNE DISEASES | ANTIGEN |
|---|---|
| Goodpasture's disease | Alpha 3 chain of type IV collagen |
| Autoimmune myocarditis | Myosin |
| Membranous nephropathy | Type-M phospholipase A2 receptor (PLA2R) |
| Autoimmune hepatitis | Cytochrome P450 1A2 |
| Ulcerative colitis | Tropomyosin isoform 5 (hTM5) |
| Crohn's disease | Major zymogen granule membrane glycoprotein 2 (GP2) |
| Multiple sclerosis | Myelin basic protein (MBP) |
| Myasthenia Gravis | Nicotinic acetylcholine receptor (AChR) |
| Neuromyelitis optica | Aquaporin-4 (AQP4) |

Table 3 below provides non-limiting examples useful antigens for various allogenic transplanted organs.

TABLE 3

| ALLOIMMUNE TRANSPLANT INTOLERANCE | ANTIGEN |
|---|---|
| Pancreas or Islet of Langerhans | GAD65 |
|  | Insulinoma Associated protein 2 (IA-2) |
| Kidney | Type-M phospholipase A2 receptor (PLA2R) |
| Heart | Myosin |
| Lung | Alpha 3 chain of type IV collagen |
| Liver | Cytochrome P450 1A2 |
| Intestine | Major zymogen granule membrane glycoprotein 2 (GP2) |
|  | Tropomyosin isoform 5 (hTM5) |

Table 4 below provides non-limiting examples of amino acid sequences of useful GAD65 epitopes.

TABLE 4

```
SEQ ID NO: 1 =      FT YEIAPVFVLL EYVTLKKMRE IIGWPGGSGD GIFSPGGAIS
CAR N (AA 39-173):  NMYAMMIARF KMFPEVKEKG MAALPRLIAF TSEHSHFSLK
                    KGAAALGIGT DSVILIKCDE RGKMIPSDLE RRILEAKQKG
                    FVPFLVSATA GTT

SEQ ID NO: 2: =     ER ANSVTWNPHK MMGVPLQCSA LLV
CAR M (AA 219-243):

SEQ ID NO: 3 =      KMFPEVKEKG MAALPRLIAF TSEHSHFSLK KGAAALGIGT
(AA 96-173):        DSVILIKCDE RGKMIPSDLE RRILEAKQKG FVPFLVSATA
                    GTT

SEQ ID NO: 4 =      AISNMYA MMIARFKMFP EVKEKGMAAL PRLIAFTSEH
(AA 244-295):       SHFSLKKGAA ALGIG

SEQ ID NO: 5 =      IKNREG YEMVFDGKP
(AA 485-499):

SEQ ID NO: 6 =      FFRMV ISNPAATHQD IDFLIEEIER LGQDL
(AA 556-585)
```

Optionally, one or both of the CAR GAD65 epitope recognizing paratopes may be comprised in a vector, which may be the same vector (bicistronic) or separate vectors. The amino acid encoding the CAR GAD65 paratopes may each be operably linked to a promoter which may be the same or different promoters. Optionally, one or both may be comprised in a vector, which may be the same vector (bicistronic) or separate vectors. The CAR GAD65 paratopes may each be operably linked to a promoter which may be the same or different promoters.

Example 1—Type 1 Diabetes

Methods:

Two GAD65 B cell epitopes that interact with two immunodominant regions in the N-terminal (CAR-N) and Middle (CAR-M) regions were selected for assembly onto T cell receptors (CD28 hinge-transmembrane-intracellular regions and CD3ξ intracellular domain).

These GAD65 CAR-Tregs were used to prevent/treat diabetes in a humanized mouse model of T1D.

Results:
Confocal images demonstrated the homing of CAR-Tregs to peri-insular areas 24 hours after intravenous immunization. 30-day follow up, fasting blood glucoses and GTT/insulin secretion tests significantly improved in GAD65 specific CAR Treg treated groups as compared to Normal Treg and non-specific EPCAM (control CAR-Treg) group. The pancreatic islet localization of GAD65 CAR-Tregs was still demonstrable at 30 days. Flow cytometry confirmed the retreat of CD8+T effector (Teff) cells and proliferation of GAD65 CAR-Tregs.

FIG. 1A provides a CAR Treg design scheme.

Figure 1B:
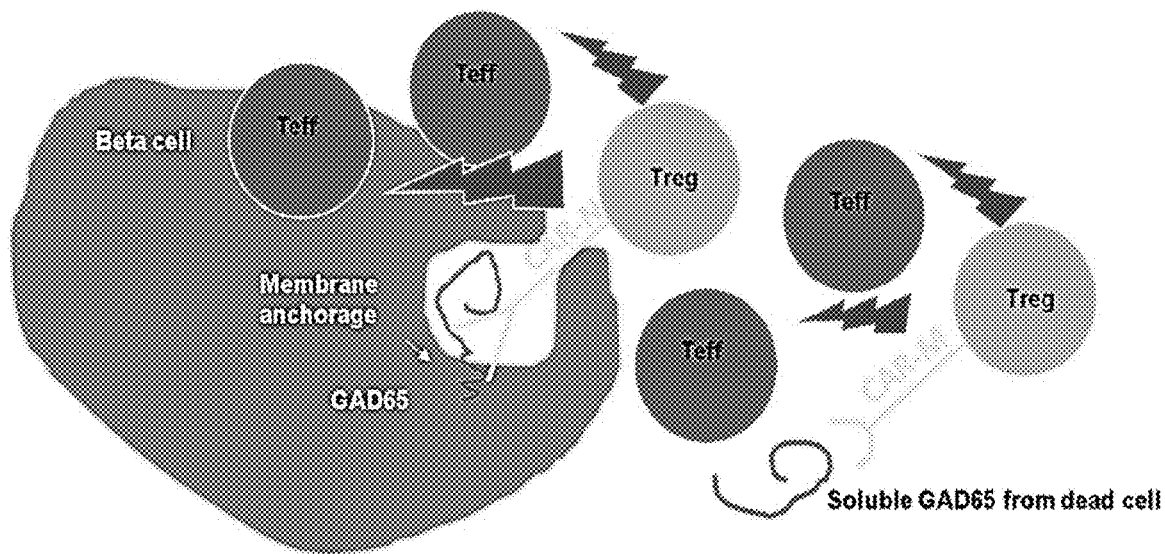
FIG. 1B: Schematic illustration of down-regulation of Teffs.

FIG. 1B schematically illustrates that, in order to downregulate Teffs, antigen-specific regulatory T cells, (CAR-Tregs) need to be abundantly present and in close proximity of beta cells. Once CAR-Tregs are activated against GAD65, the CAR-Tregs silence nearby Teffs cells and rescue the pancreatic islet beta cells.

Figure 2:
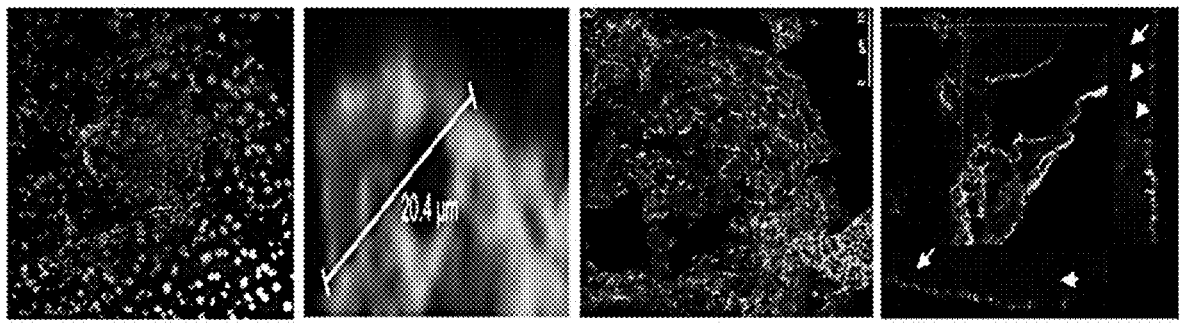
FIG. 2: Humanized mouse model of T1D—Comparison between of human and mouse model genetic predisposition and target antigen availability; and confocal microscopy of humanized T1D mouse pancreatic frozen sections (8 µm). Red=insulin; Blue=GAD65; Green=HLA-DQ8.

FIG. 2 shows the characteristics of a humanized mouse model of T1D. In the top panel of FIG. 2, is a comparison between of human and mouse model genetic predisposition and target antigen availability. In the bottom panel of FIG. 2 is the confocal microscopy of humanized T1D mouse pancreatic frozen sections (8 μm). Red=insulin; Blue=GAD65; Green=HLA-DQ8. Left picture shows pancreatic islet. GAD65 seems to be present in and around insular area, but also is in close contact with APCs (HLA-DQ8). Left-mid picture, GAD65 (blue) is recognized and engulfed by macrophages (green 20.4 μm) beta cells were stained with insulin (red). Right pictures show progressively higher magnification (from right to left) of T1D mice peri-islet area. White arrows indicate GAD65 (beta cells) and APC HLA-DQ8 interaction.

Figure 3:
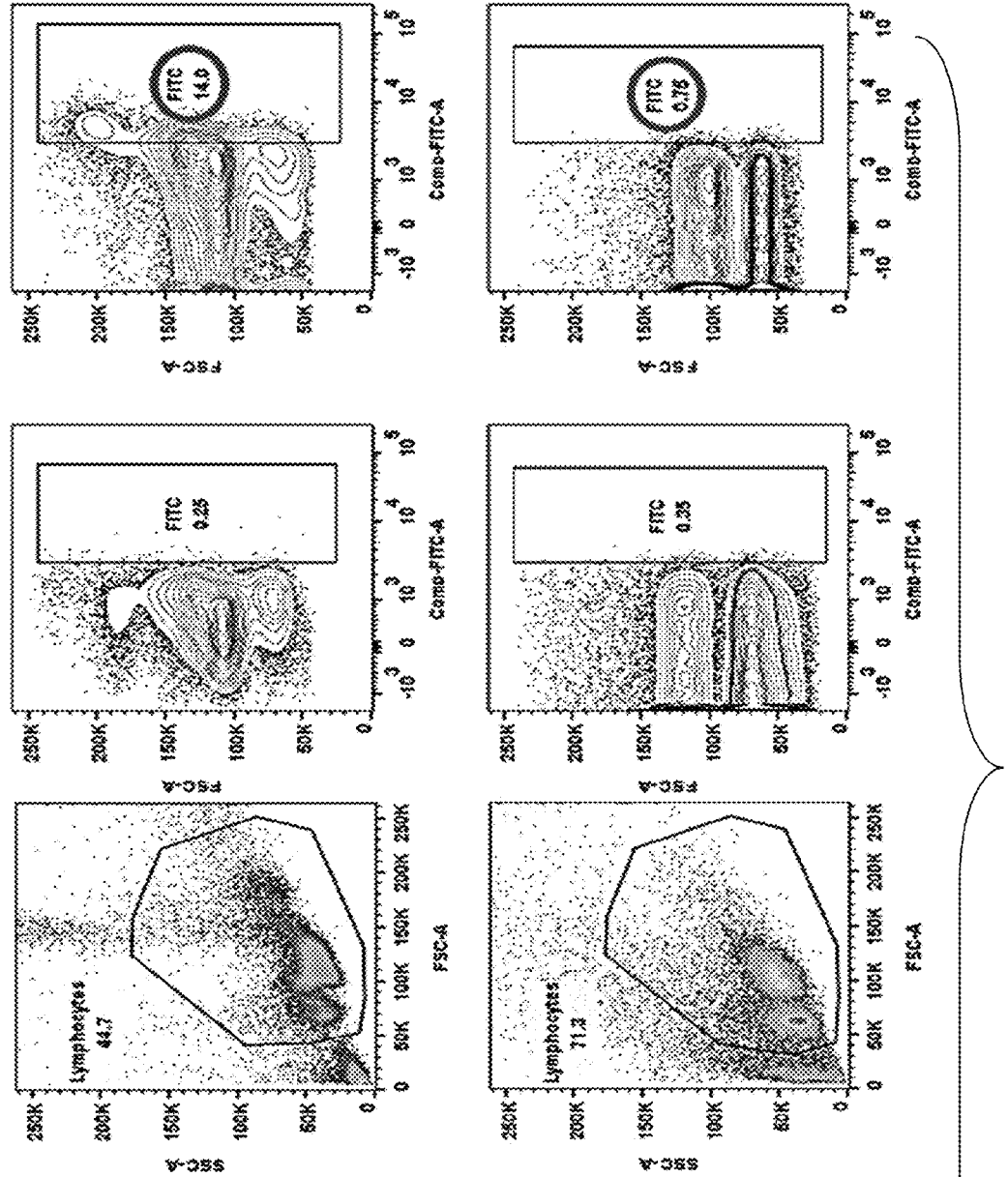
FIG. 3. Flow cytometry tracking of GFP-GAD65 CAR-Treg cells in Blood, Pancreatic Lymph Nodes (PLN), Pancreas (PN) and Spleen. Single cells were acquired using Flow Cytometer (BD FACSCANTO) for detecting GFP in FITC channel. Spontaneous humanized mouse model was infused with 5 million GFP-GAD65 CAR-Treg cells (co-expressing Green Fluorescent Protein (GFP), 24 hrs before sacrifice).
Figure 3:
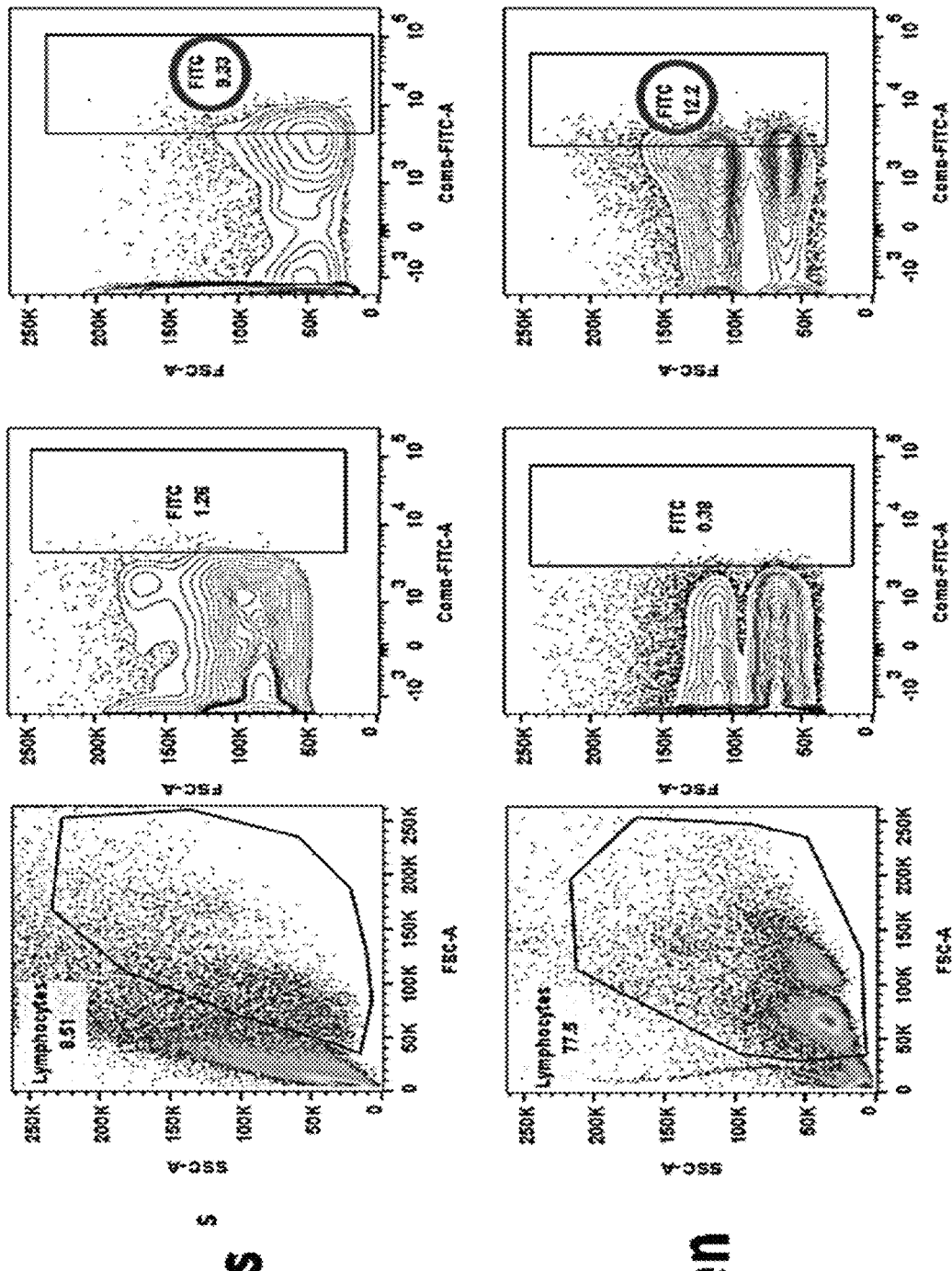

FIG. 3 shows the flow cytometry tracking of GFP-GAD65 CAR-Treg cells in Blood, Pancreatic Lymph Nodes (PLN), Pancreas (PN) and Spleen. Single cells were acquired using Flow Cytometer (BD FACSCANTO) for detecting GFP in FITC channel. Spontaneous humanized mouse model was infused with 5 million GFP-GAD65 CAR-Treg cells (co-expressing Green Fluorescent Protein (GFP), 24 hrs before sacrifice).

Figure 4:
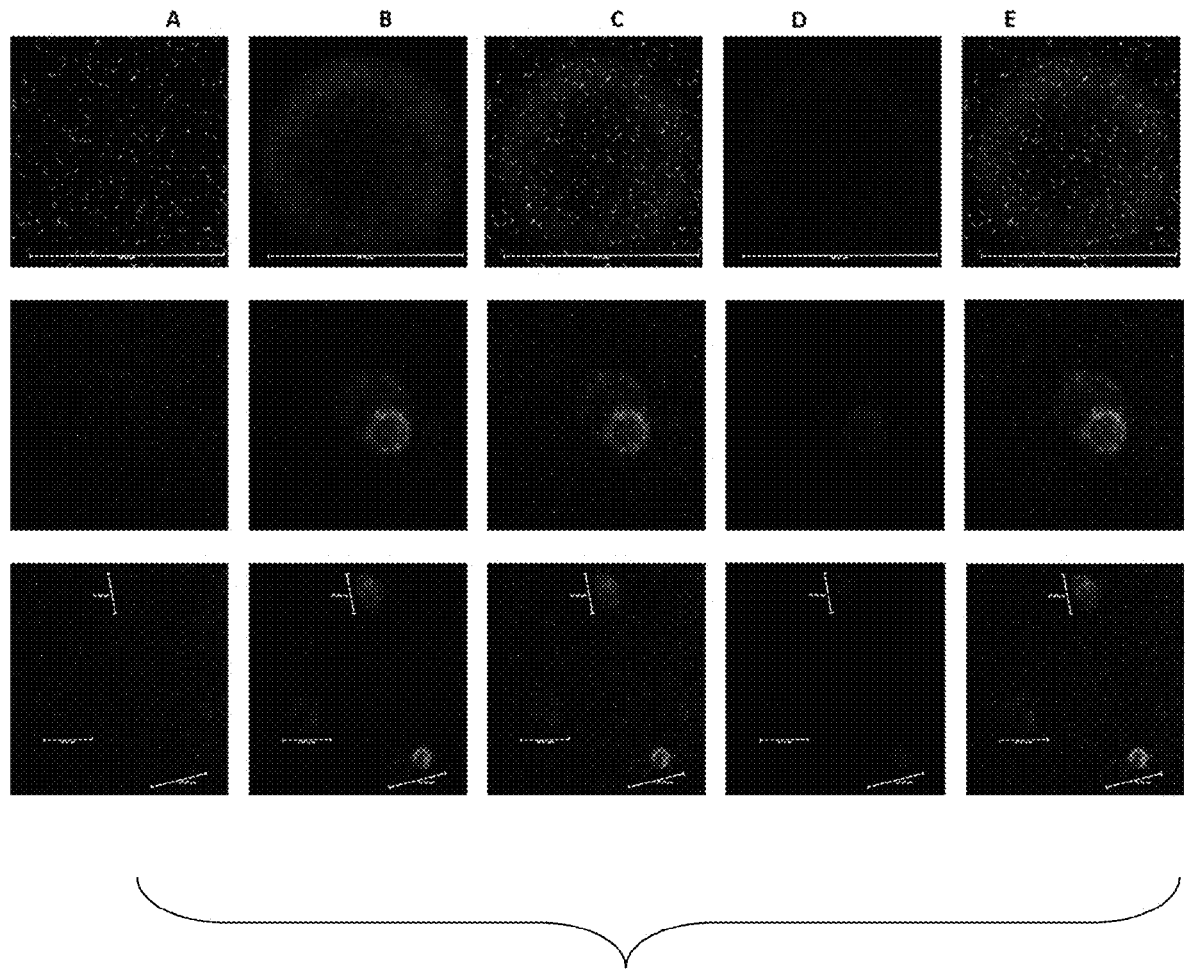
FIG. 4. 3D iDISCO. Morphology of pancreatic islets and localization of CAR-Treg cells. Top to bottom: Islet magnification (100×), (10×), (4×). A. Green=GFP, B. Red=Insulin, C. Overlay of A and B, D. Blue=GAD65, E. Overlay of A, B and D.

FIG. 4 shows 3D iDISCO and the morphology of pancreatic islets and localization of GFP-GAD65 CAR-Treg cells. Humanized mice (T1D model) were injected with CAR-Treg cells (expressing Green Fluorescent Protein, GFP) and euthanized 24 hours after.

In FIG. 4, from top to bottom (three different magnifications of pancreas 100×, 10× and 4×): Islets were individually recorded at 3 different locations (lower panel, 4× magnification).

In FIG. 4, from left to right (stains):
Column A: Green filter shows CAR-Treg cells expressing GFP.
Column B: Red filter shows Insulin expressing islet cells.
Column C: Overlay of A and B.
Column D: Blue filter shows GAD65 expressing islet cells.
Column E: Overlay of A, B and D.

FIGS. 5A-5E contain a series of graphs showing flow cytometry of immune cells. Immune cell profiling of different CAR-Tregs and control cells treated animals: Autologous Tregs were isolated from spleen and amplified in vitro using IL-2 (2000 ng/ml). Autologous, amplified Tregs were then transduced with CAR-M and CAR-N Treg constructs. Treg expression of CAR-M/N constructs was confirmed by PCR and western blot. Humanized mice (T1D model) were treated with 5 million GAD65 specific CAR-M Treg/ CAR-N Treg cells, Normal Treg cells and EPCAM (control CAR-Treg cells). The mice were euthanized after 30 days post-treatment. Pancreas (PN), Pancreatic Lymph Nodes (PLN) and Spleens were processed into single cell suspensions.

Figure 5A:
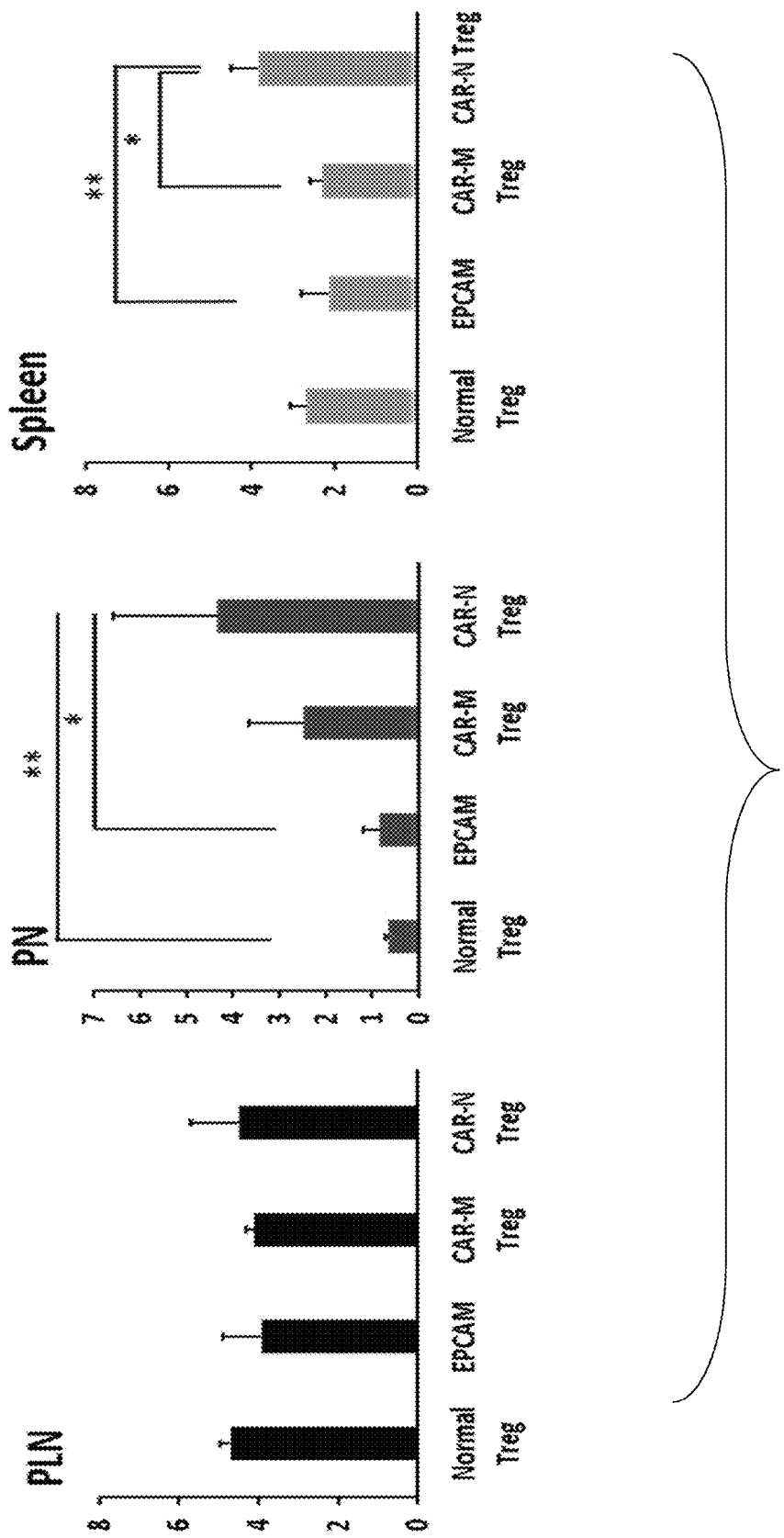
FIGS. 5A-5E. Flow Cytometry. Immune cell profiling of different CAR-Tregs and normal Treg cells treated animals.

FIG. 5A: Treg cell population at Pancreatic Lymph nodes (PLN), Pancreas (PN), and Spleens 30 days post-treatment with either Normal Treg, EPCAM (control CAR-Treg), GAD65 CAR-M or CAR-N Treg cells. Statistical significance (* and **) was determined at P<0.05.

Figure 5B:
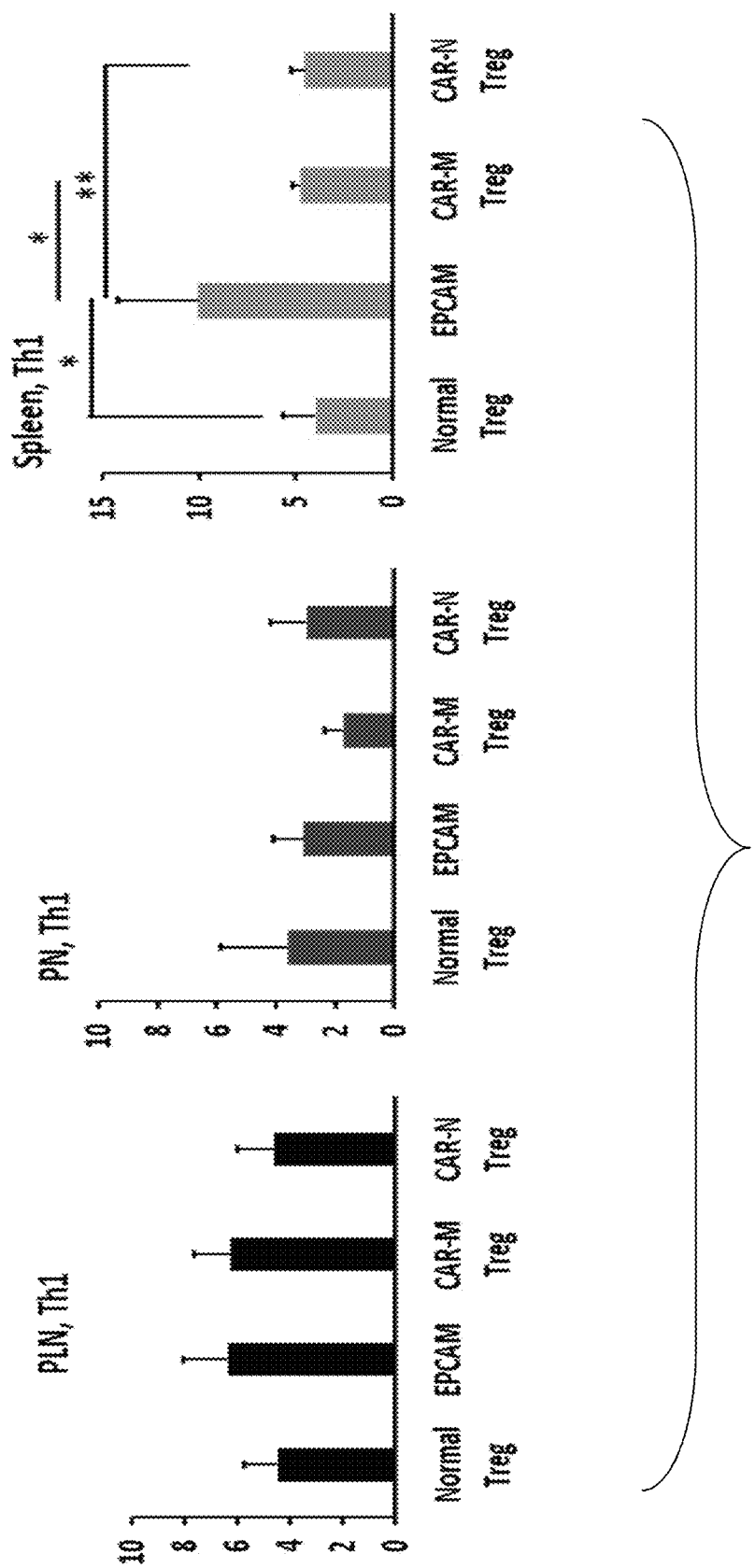

FIG. 5B: T helper (Th1) cell population at Pancreatic Lymph Nodes (PLN), Pancreas (PN), and Spleens 30 days post-infusion. Statistical significance (* and **) was determined at P<0.05.

Figure 5C:
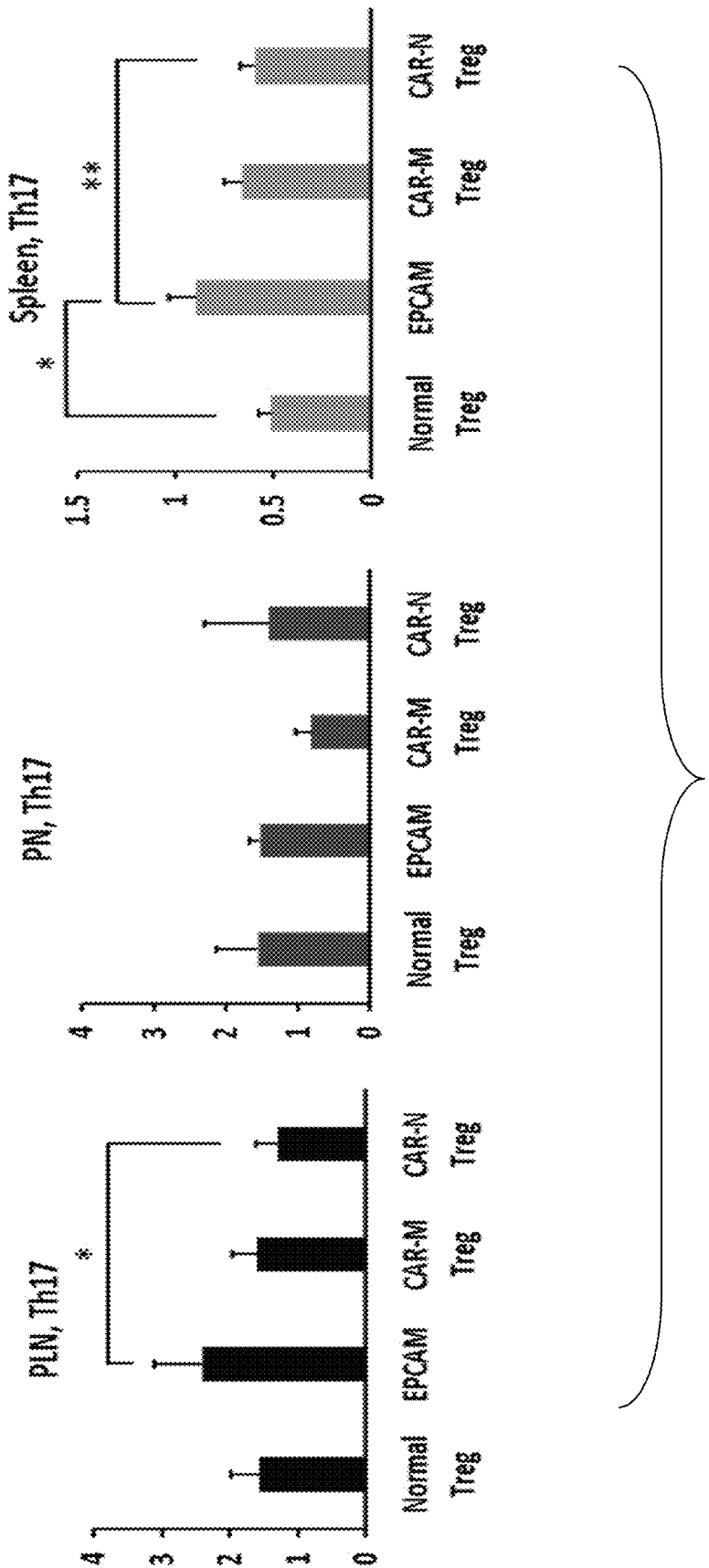

FIG. 5C: T helper (Th17) cell population at Pancreatic Lymph Nodes (PLN), Pancreas (PN), and Spleens 30 days post-infusion. Statistical significance (* and **) was determined at P<0.05.

Figure 5D:
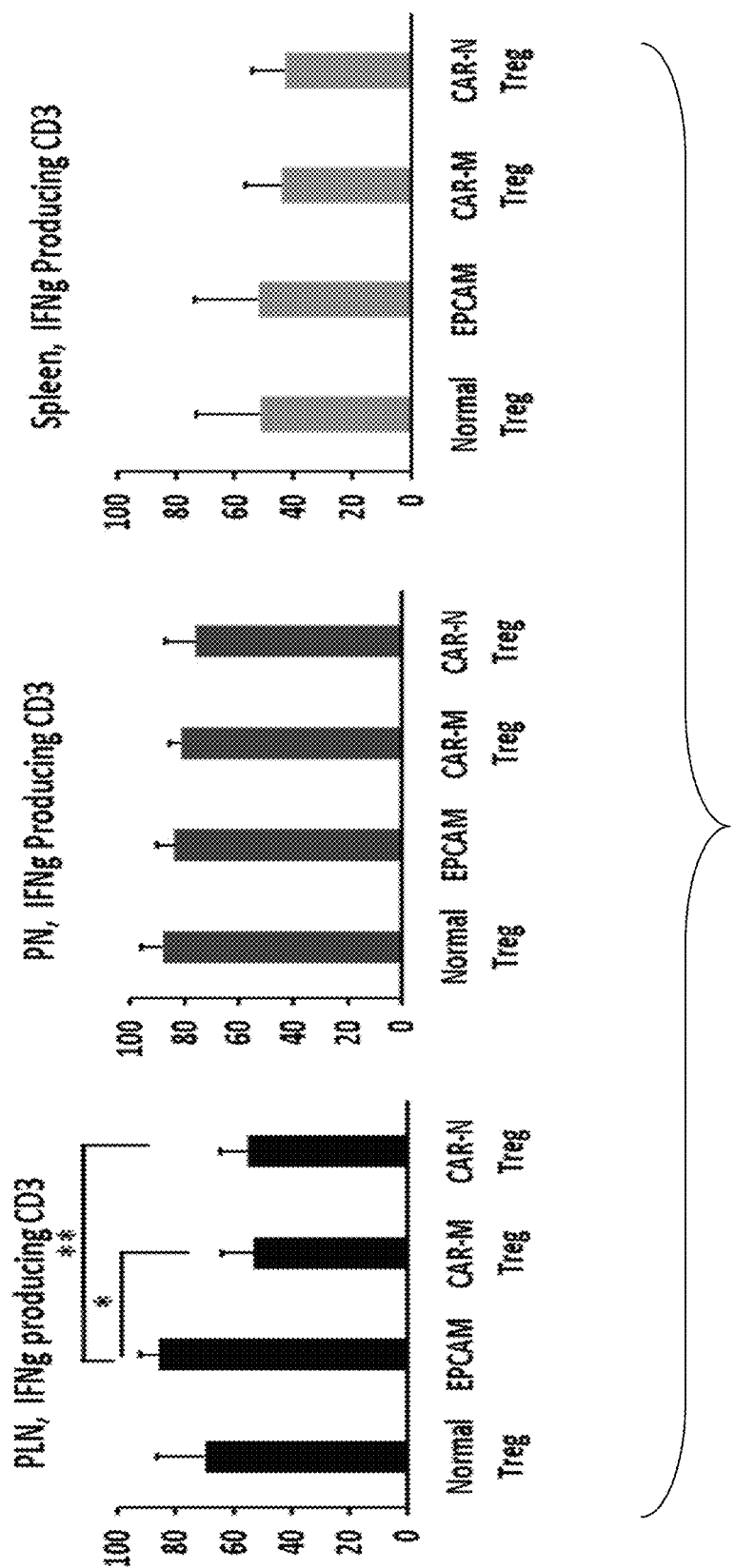

FIG. 5D: Interferon gamma (IFNg) producing T cells (CD3) cell population at Pancreatic Lymph Nodes (PLN), Pancreas (PN), and Spleens 30 days post-infusion. Statistical significance (* and **) was determined at P<0.05.

Figure 5E:
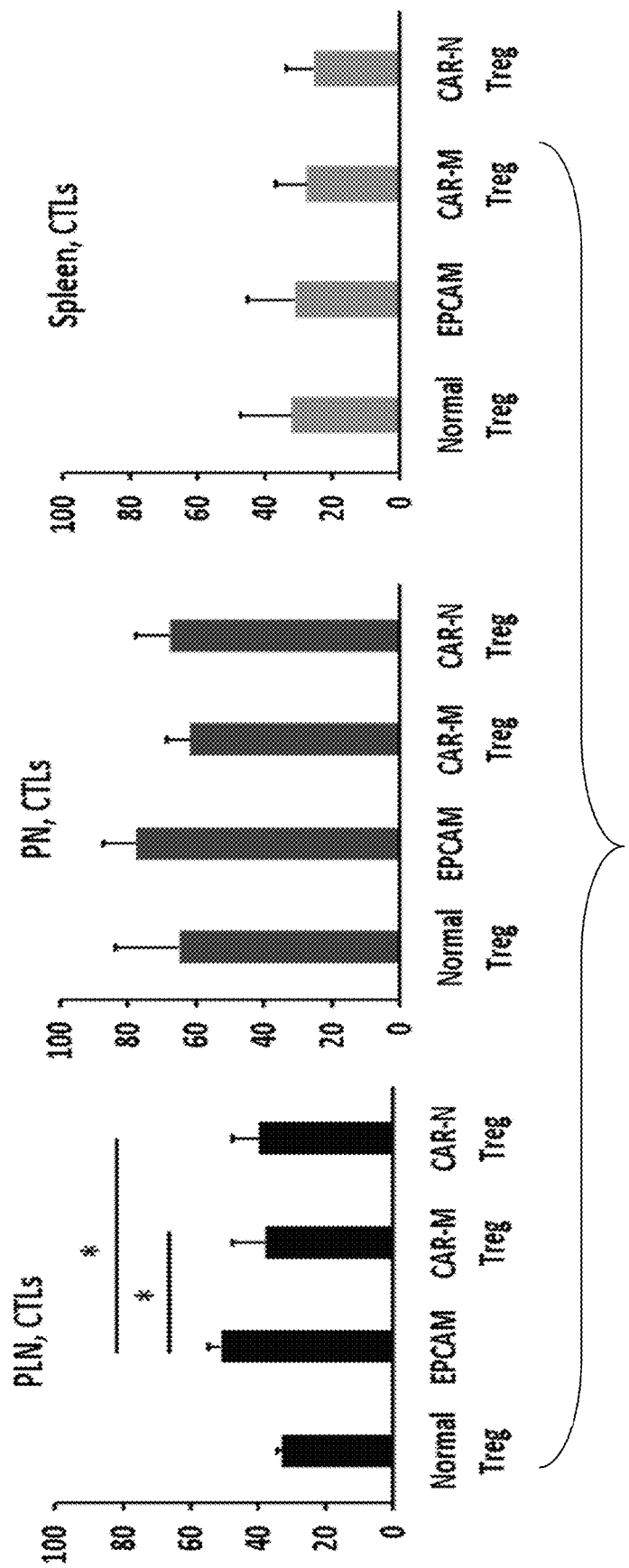

FIG. 5E: Interferon gamma (IFNg) producing CD8 T cell (CTLs) population at Pancreatic Lymph Nodes (PLN), Pancreas (PN), and Spleens 30 days post-infusion. Statistical significance (* and **) was determined at P<0.05.

Figure 6:
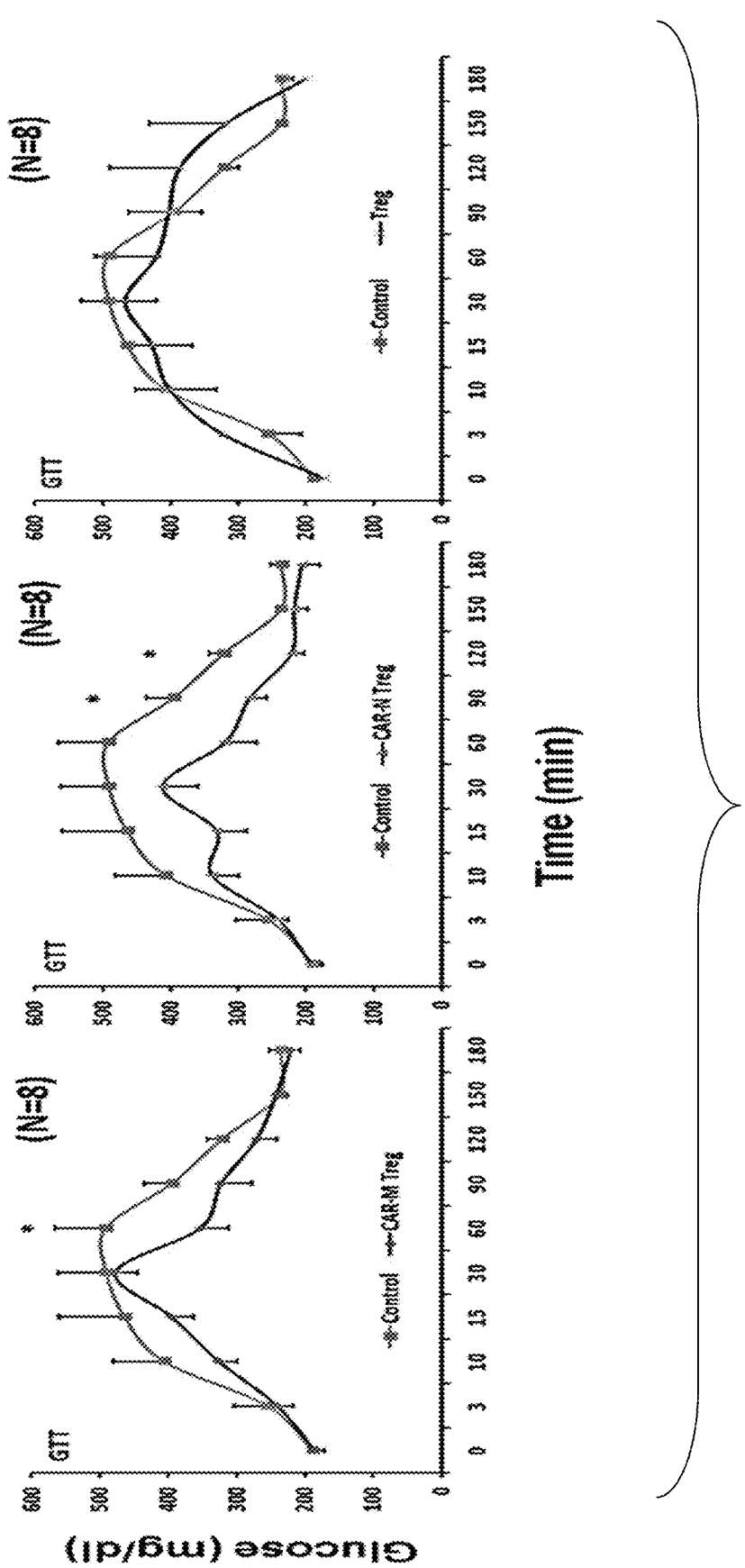
FIG. 6. Glucose tolerance test (GTT) readings after one month of CAR-M Treg/CAR-N Treg/Normal Treg/Non islet specific CAR-Treg (EPCAM) treatment. 30-day follow up GTT. Glucose tolerances significantly improved in GAD65 specific CAR Treg treated groups as compared to Normal Treg and non-specific EPCAM (control CAR-Treg) group. Normal Treg treatment shows no difference when compared to non-islet specific EPCAM (control CAR-Treg) group.

FIG. 6 shows glucose tolerance test (GTT) readings after one month of CAR-M Treg/CAR-N Treg/Normal Treg/ EPCAM (control CAR-Treg) treatment. 30-day follow up GTT: Glucose tolerances significantly improved in GAD65 specific CAR Treg treated group as compared to Normal Treg and non-specific EPCAM (control CAR-Treg) group. Normal Treg treatment shows no difference when compared to EPCAM (control CAR-Treg).

Figure 7A:
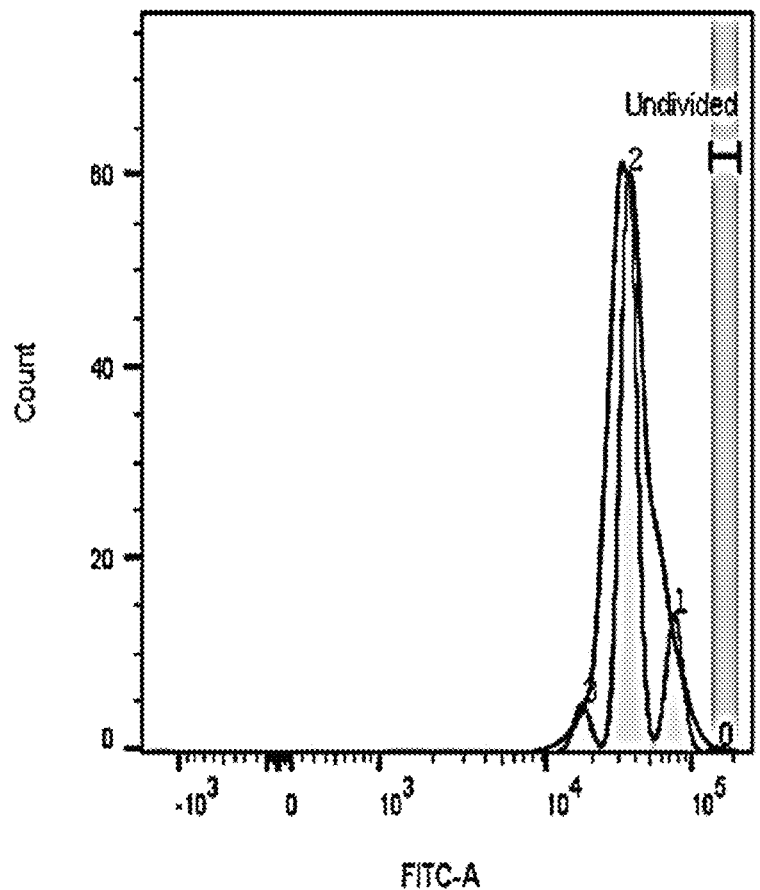
FIGS. 7A-7B: Suppression/proliferation assay of CAR-Treg (CD25+) and Tresp (CD4+CD25−) (n=3-4)
Figure 7B:
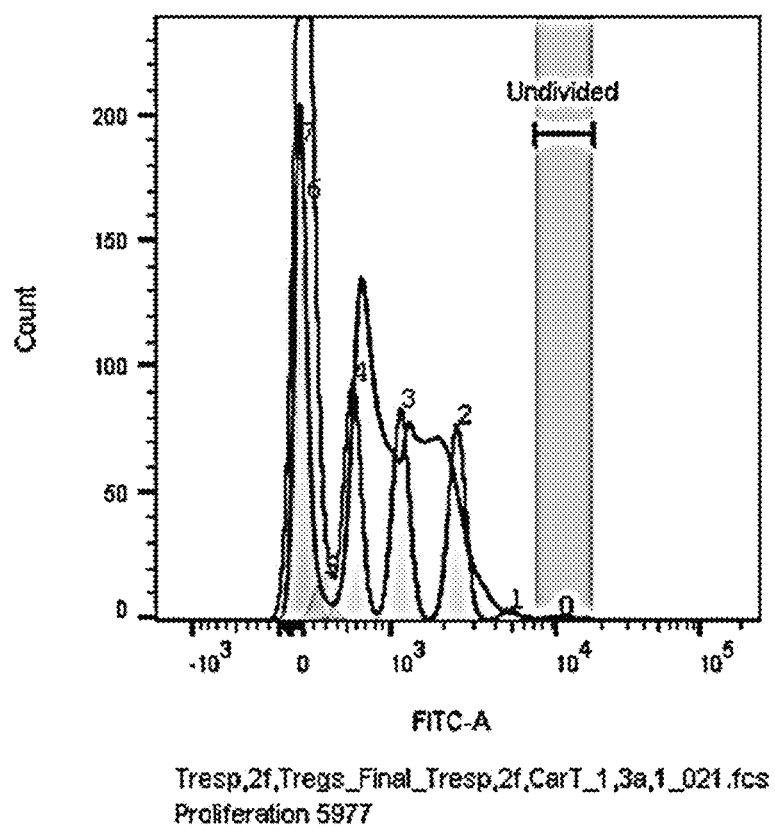

FIGS. 7A-7B shows the suppression/proliferation assay of CAR-Treg (CD25+) and Tresp (CD4+CD25−) (n=3-4): FIG. 7A=Treg. (CD4+CD25+); FIG. 7B=CAR-Treg (CD25+). Flow cytometry analysis of an in vitro suppression assay: Naïve CD4 T cells used as responder T cells (Tresp CD4+CD25−) and GAD65 CAR-Treg cells (CD25+) were co-cultured in different ratios (Table in FIG. 7C) with recombinant hGAD65 antigen (4 μg/ml). After 5 days, cells were immunofluorescently stained with CD4 and CD25 antibodies. Lymphocytes were gated according to FSC and SSC. CD4 T cells were gated according to CD4 (y-axis) and FSC (x-axis). CAR-Treg cells (CD25+) were distinguished from the CD4+CD25− Tresp cells according to CD25 (y-axis). Both cell populations were incubated in CellTrace (CFSE-FITC, x-axis). Histogram plots show proliferation index/replication index as analyzed by using FLOW JO_V10 proliferation assay software.

Figure 7C:
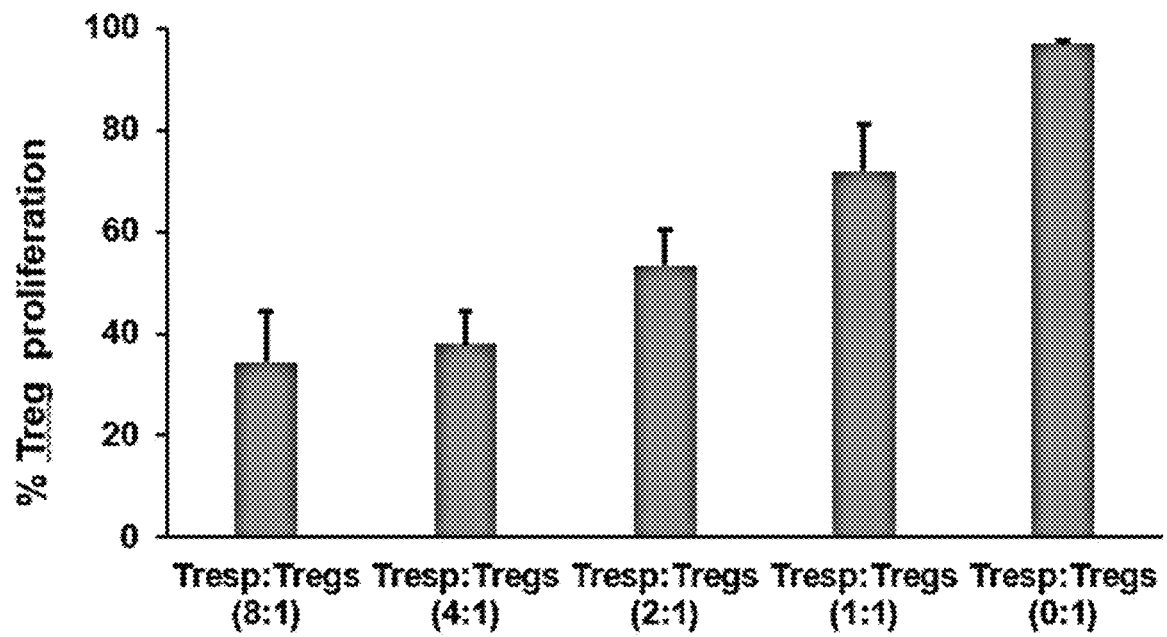
FIG. 7C: Percent Treg proliferation.

FIG. 7C is a summarized data of in vitro suppression assay. Tresp cells (CD4+CD25−, isolated from mouse spleen by using CD4 T Cell Isolation Kit) and GAD65 specific CAR-Treg cells (CD25+) were co-cultured in presence of recombinant hGAD65 antigen (4 μg/ml) for 5 days. The suppressive/proliferative capacity of the cells was determined by analyzing the proliferation of GAD65 CAR-Treg and Tresp cells under different co-culture ratios.

Figure 7D:
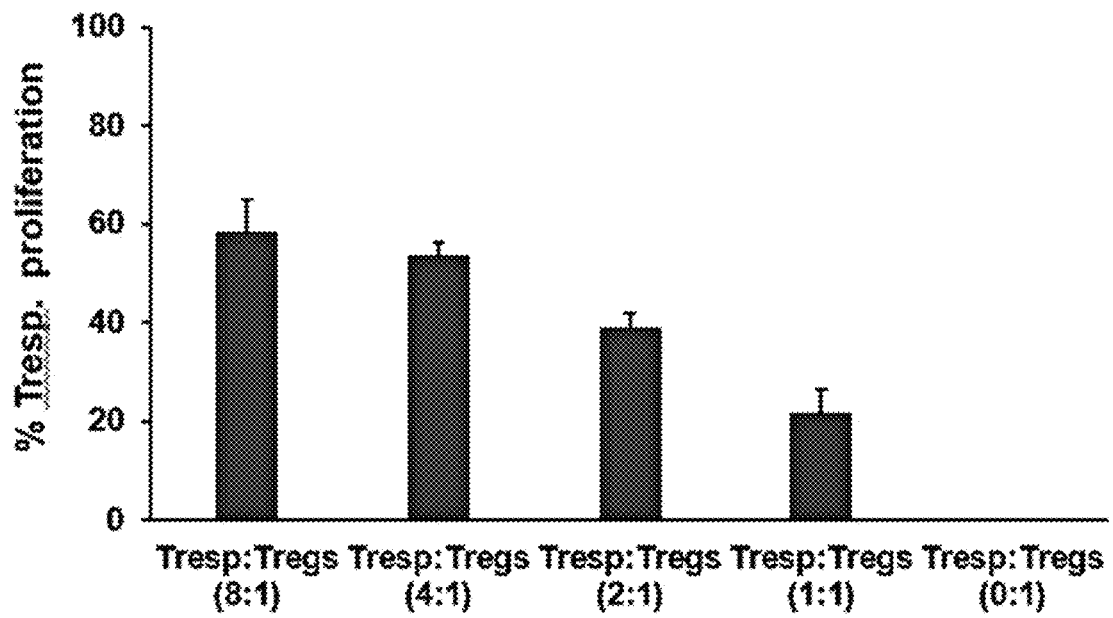
FIG. 7D: Percent Tresp proliferation.

FIG. 7D: Table of summarized data of proliferative/ replicative index in vitro suppression/proliferation assay at different ratios of Tresp and CAR-Treg, as depicted in FIG. 7A-7B.

Figure 8A:
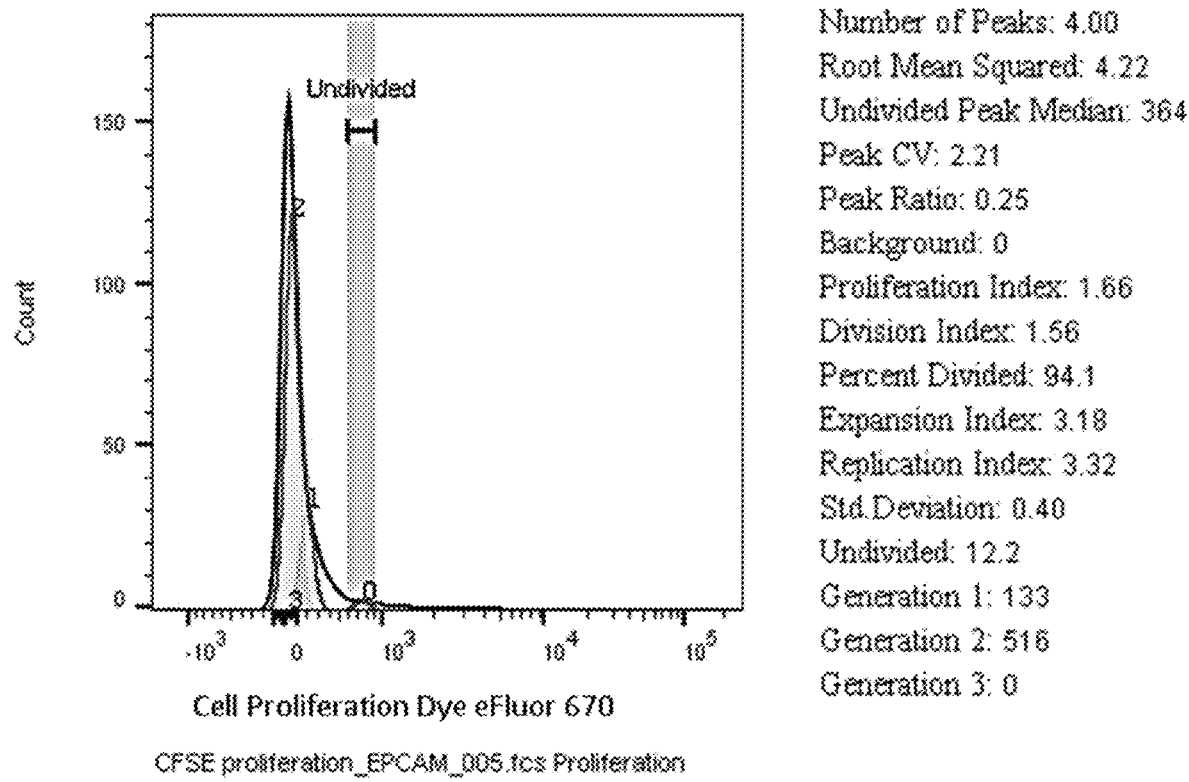
FIGS. 8A-8B: Analysis of in vivo proliferation assay: EPCAM specific CAR-Tregs cells (FIG. 8A) and GAD65 specific CAR-Tregs cells (FIG. 8B).
Figure 8B:
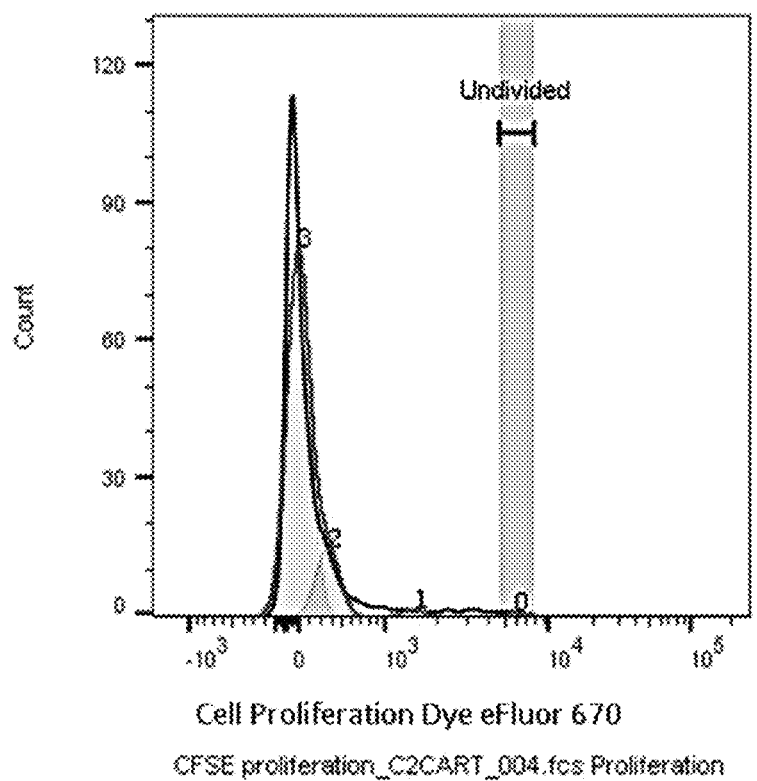

FIGS. 8A-8B show an analysis of in vivo proliferation assay: EPCAM specific CAR-Tregs cells and GAD65 specific CAR-Tregs cells co-expressing green fluorescent protein (GFP) were infused into the humanized T1D mice. Mice were sacrificed after 48 hrs. CAR-Tregs (EPCAM and GAD65) were isolated on the basis of GFP co-expression. Both cell populations were incubated in (Cell Proliferation Dye eFluor 670). These cells were analyzed in BD Canto flow cytometry, lymphocytes were gated according to FSC and SSC. CAR-Treg cells were further gated on the basis of CD25+ve cells (y-axis) and Cell Proliferation Dye eFluor 670 (x-axis).

The frequency of proliferating cells was analyzed by using FLOW JO proliferation assay. Histogram plots were used to determine the proliferation index/replication index. In-vivo proliferation of GAD65 specific CAR-Treg cells comparatively doubled non-diabetic CAR-Treg (EPCAM). This shows the specificity of GAD65 CAR Tregs and their proliferative capacity in an antigen-specific manner.

Figure 8C:
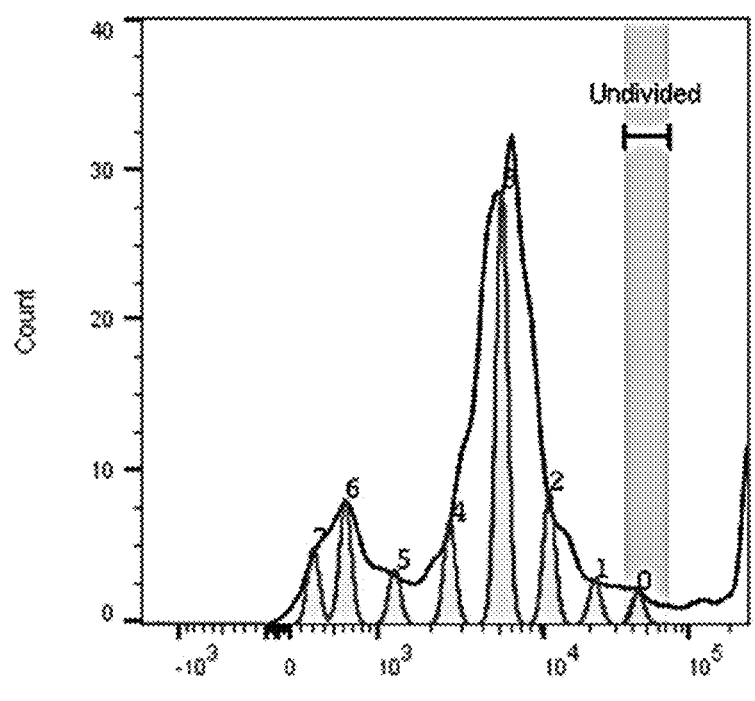
FIGS. 8C-8D: Analysis of an in vitro proliferation assay: Treg cells (FIG. 8C) and CAR-Treg cells (FIG. 8D).
Figure 8D:
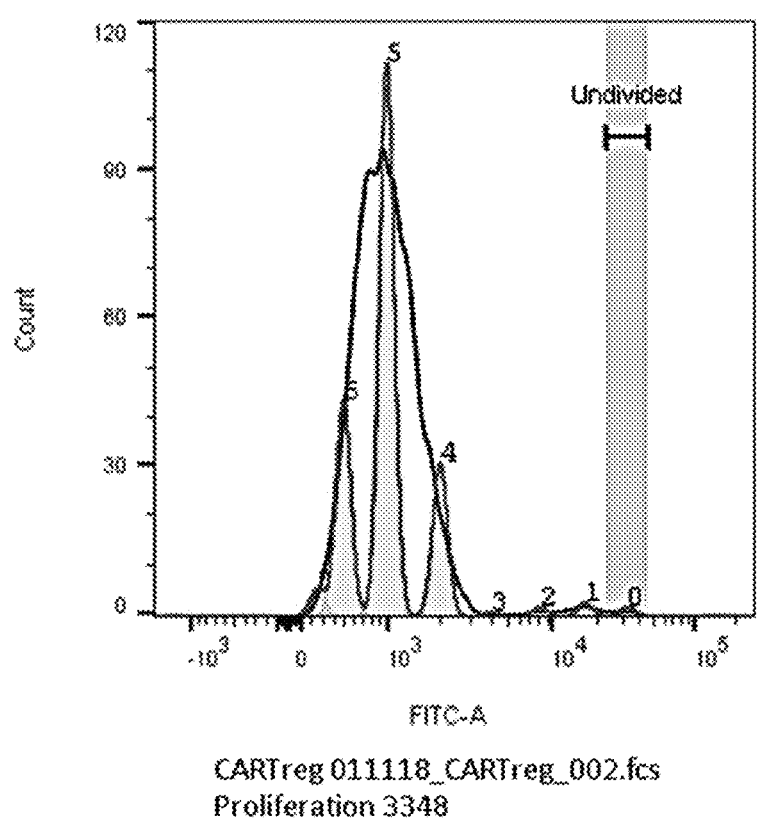

FIGS. 8C-8D show an analysis of an in vitro proliferation assay: Normal Treg cells (FIG. 8C) and GAD65 CAR-Treg cells (FIG. 8D) proliferated under high concentration of IL-2 (2000 ng/ml) and recombinant hGAD65 (4 µg/ml). Lymphocytes were gated according to FSC and SSC. Treg cells (CD25+ve) were distinguished from the CD25−ve cells (y-axis). Both cell populations were incubated in CellTrace (CFSE-FITC, x-axis).

The frequency of proliferating cells was analyzed by using FLOW JO proliferation assay. Histogram plots were used to determine the proliferation index/replication index. CAR-Tregs are specific to GAD65 antigen and their proliferation rate was almost 3 times that of Normal Treg cells.

Thus, antigen-specific Treg re-direction and expansion using antigen-specific CAR-Tregs and consequent Teff downregulation allows for recovery and reconstitution of beta cells and are expected to behave similarly in humans as well.

It is to be understood that Teff includes: CD4, T helper 1, T helper 17, CD8, and Cytotoxic lymphocytes (CTLs).

Examples of Prevention and/or Treatment of T1D

In some embodiments, the subject has been diagnosed with T1D or IDDM, or pre-IDDM or pre-T1D. One of skill in the art can determine the patients who would potentially benefit from a therapeutic agent that would reduce or prevent the development of overt diabetes. One of skill in the art can determine the therapeutically effective amount of the composition to be administered to a subject based upon several considerations, such as local effects, pharmacodynamics, absorption, metabolism, method of delivery, age, weight, disease severity and response to the therapy.

An improvement in diabetic parameters may be any observable or measurable improvement. Thus, one of skill in the art realizes that a treatment may improve the patient or subject's condition, but may not be a complete cure of the disease. In certain aspects, the composition is administered in an effective amount to decrease, reduce, inhibit or abrogate levels of immune responses against the host's tissues and/or the donor's organs rejections.

Efficacy may be monitored in a patient during treatment, e.g., by monitoring weight, where weight gain of at least about 5%, at least about 10%, at least about 15% or more can indicate successful treatment. Measurement of insulin is another relevant marker for monitoring efficacy, where an increase in value may be at least about 10%, at least about 25%, at least about 50% or more with successful therapy.

In an embodiment of the present invention, the engineered Treg composition is administered in an effective amount to decrease, reduce, inhibit or abrogate inflammation and toxicity.

Treatment regimens may vary as well, and often depend on the health and age of the patient. Certain types of disease will require more aggressive treatment, while at the same time, certain patients cannot tolerate more toxic regimens. The clinician will be best suited to make such decisions based on the known efficacy and toxicity (if any) of the therapeutic formulations.

In specific embodiments, the composition is given in a single dose or multiple doses. The single dose may be administered daily, or multiple times a day, or multiple times a week, or monthly or multiple times a month, or once in a month/year. A series of doses may be administered daily, or multiple times a day, weekly, or multiple times a week, or monthly, or multiple times a month.

The improvement is any observable or measurable improvement. Thus, one of skill in the art realizes that a treatment may improve the patient or subject's condition, but may not be a complete cure of the disease. In certain aspects, the composition is administered in an effective amount to decrease, reduce, inhibit or abrogate levels of an immune response of the recipient.

The composition of the present invention may precede, be co-current with and/or follow the other agent(s) by intervals ranging from minutes to weeks. In embodiments where the composition and other agent(s) are applied separately to a cell, tissue or organism, one would generally ensure that a significant period of time did not expire between the time of each delivery, such that the composition and agent(s) would still be able to exert an advantageously combined effect on the cell, tissue or organism.

Various combination regimens of the composition and one or more agents are employed. One of skill in the art is aware that the composition of the present invention and agents can be administered in any order or combination.

Administration

Compositions comprising genetically modified immunoresponsive cells described herein can be provided systemically or directly to a subject for the treatment of autoimmune disorders or diseases. In one embodiment, such cells are directly injected into an organ of interest (e.g., transplanted organ, organ affected by autoimmune disorder, etc.).

Alternatively, compositions comprising genetically modified immunoresponsive cells are provided indirectly to the organ of interest, for example, by administration into the circulatory system (e.g., the vasculature). Expansion and differentiation agents can be provided prior to, during or after administration of the cells to increase production off cells in vitro or in vivo.

The modified cells can be administered in any physiologically acceptable vehicle, normally intravascularly, although they may also be introduced into bone or other convenient site where the cells may find an appropriate site for regeneration and differentiation (e.g., thymus).

For example, at least $1 \times 10^5$ cells will be administered, eventually reaching $1 \times 10^{10}$ or more. Genetically modified immunoresponsive cells can comprise a purified population of cells. Those skilled in the art can readily determine the percentage of genetically modified immunoresponsive cells in a population using various well-known methods, such as fluorescence activated cell sorting (FACS). Preferable ranges of purity in populations comprising genetically modified immunoresponsive cells are about 50 to about 55%, about 55 to about 60%, and about 65 to about 70%. More preferably the purity is about 70 to about 75%, about 75 to about 80%, about 80 to about 85%; and still more preferably the purity is about 85 to about 90%, about 90 to about 95%, and about 95 to about 100%.

Dosages can be readily adjusted by those skilled in the art (e.g., a decrease in purity may require an increase in dosage).

The cells can be introduced by injection, catheter, or the like. If desired, factors can also be included, including, but not limited to, interleukins, e.g. IL-2, IL-3, IL-6, IL-10, IL12, IL13, IL21, IL1S as well as the other interleukins, the colony stimulating factors, such as G-, M- and GM-CSF, interferons, e.g. γ-interferon and erythropoietin.

Compositions of the invention include pharmaceutical compositions comprising genetically modified immunoresponsive cells or their progenitors and a pharmaceutically acceptable carrier. Administration can be autologous or heterologous. For example, immunoresponsive cells, or progenitors can be obtained from one subject, and administered to the same subject or a different, compatible subject. Peripheral blood derived immunoresponsive cells of the invention or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing genetically modified immunoresponsive cells), it will generally be formulated in a unit dosage injectable form (solution, suspension, emulsion).

Pharmaceutical Compositions

Pharmaceutical compositions of the present disclosure comprise an effective amount of a compound disclosed herein, and/or additional agents, dissolved or dispersed in a pharmaceutically acceptable carrier. The phrases "pharmaceutical" or "pharmacologically acceptable" refers to molecular entities and compositions that produce no adverse, allergic or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety and purity standards as required by FDA Office of Biological Standards.

A composition disclosed herein may comprise different types of carriers depending on whether it is to be administered in solid, liquid or aerosol form, and whether it need to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound (e.g., cell mixture). In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples (e.g. weight-based active compound), a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543, 158; 5,641,515; and 5,399,363 are each specifically incorporated herein by reference in their entirety).

Solutions of the compositions disclosed herein (e.g., cellular mixture) may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In most cases, the form must be sterile and must be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it is preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose for the cell mixture. These particular aqueous solutions are especially suitable for intravenous, intramuscular, subcutaneous, and intraperitoneal administration. In this connection, sterile aqueous media that can be employed is known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroethylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Kits

It is further intended the compounds disclosed herein could be packaged in the form of a kit containing a single or separate containers. Many embodiments of such kits are possible. For instance, a kit could house two containers, the first container comprising a compound of Formula I, and the second container comprising a compound of Formula II. By way of further non-limiting example, a kit could have a first container housing a solution comprising one or more compounds of Formula I and Formula II, and a second container comprising a syringe configured to inject the solution. As another example, a kit for the preparation of a pharmaceutical composition could have a first container housing one or more compounds of Formula I and Formula II, and a second container housing a pharmaceutically acceptable carrier, excipient, diluent, or adjuvant. Many other variations and embodiments of such kits are envisioned. The kits typically further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

The publication and other material used herein to illuminate the invention or provide additional details respecting the practice of the invention, are incorporated by reference herein, and for convenience are provided in the following bibliography.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

What is claimed is:

1. An immunoresponsive cell comprising:
 a chimeric antigen receptor (CAR) that binds to glutamic acid decarboxylase 65 kDA (GAD65);
 the CAR comprising:
 a) an intracellular signaling domain of a CD37 polypeptide and an intracellular signaling domain of CD28 hinge-transmembrane-intracellular region, and
 b) an extracellular polypeptide which is a GAD65 monoclonal antibody (MAb) antigen binding domain and which recognizes at least a part of an amino acid sequence selected from the amino acids having SEQ ID Nos: 1-6; or, at least one complete amino acid sequence selected from the amino acids having SEQ ID Nos: 1-6; and
 wherein the immunoresponsive cell is a regulatory T cell.

2. The immunoresponsive cell of claim 1, wherein the MAb antigen binding domain enhances an immune response in a subject by binding specific antigens in a target cell.

3. The immunoresponsive cell of claim 2, wherein the target cell is a cell in a subject that is affected by an autoimmune endocrinopathy, an organ-specific autoimmune disease, or an alloimmune transplant intolerance.

4. The immunoresponsive cell of claim 1, wherein the extracellular polypeptide recognizes an amino acid sequence having SEQ ID No: 1.

5. The immunoresponsive cell of claim 1, wherein the extracellular polypeptide recognizes an amino acid sequence having SEQ ID No: 2.

6. The immunoresponsive cell of claim 1, wherein the extracellular polypeptide recognizes an amino acid sequence having SEQ ID No: 3.

7. The immunoresponsive cell of claim 1, wherein the extracellular polypeptide recognizes an amino acid sequence having SEQ ID No: 4.

8. The immunoresponsive cell of claim 1, wherein the extracellular polypeptide recognizes an amino acid sequence having SEQ ID No: 5.

9. The immunoresponsive cell of claim 1, wherein the extracellular polypeptide recognizes an amino acid sequence having SEQ ID No: 6.

10. A pharmaceutical composition comprising an effective amount of an immunoresponsive cell of claim 1 and a pharmaceutically acceptable excipient.

11. A method of lengthening survival of a subject having type 1 diabetes (T1D), the method comprising:
 administering to the subject an effective amount of the immunoresponsive cell of claim 1, thereby lengthening survival of the subject.

12. The method of claim 11, wherein the subject is a human.

13. A method of preventing or treating type 1 diabetes (T1D), the method comprising:
 administering to the subject an effective amount of the immunoresponsive cell of claim 1, thereby treating or preventing the T1D in the subject.

14. The method of claim 13, wherein the subject is a human.

* * * * *

SEQUENCE LISTING

```
<160> NUMBER OF SEQ ID NOS: 6

<210> SEQ ID NO 1
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Phe Thr Tyr Glu Ile Ala Pro Val Phe Val Leu Leu Glu Tyr Val Thr
1               5                   10                  15

Leu Lys Lys Met Arg Glu Ile Ile Gly Trp Pro Gly Gly Ser Gly Asp
            20                  25                  30

Gly Ile Phe Ser Pro Gly Gly Ala Ile Ser Asn Met Tyr Ala Met Met
        35                  40                  45

Ile Ala Arg Phe Lys Met Phe Pro Glu Val Lys Glu Lys Gly Met Ala
    50                  55                  60

Ala Leu Pro Arg Leu Ile Ala Phe Thr Ser Glu His Ser His Phe Ser
65                  70                  75                  80

Leu Lys Lys Gly Ala Ala Ala Leu Gly Ile Gly Thr Asp Ser Val Ile
            85                  90                  95

Leu Ile Lys Cys Asp Glu Arg Gly Lys Met Ile Pro Ser Asp Leu Glu
            100                 105                 110

Arg Arg Ile Leu Glu Ala Lys Gln Lys Gly Phe Val Pro Phe Leu Val
            115                 120                 125

Ser Ala Thr Ala Gly Thr Thr
            130                 135

<210> SEQ ID NO 2
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2
```

```
Glu Arg Ala Asn Ser Val Thr Trp Asn Pro His Lys Met Met Gly Val
1               5                   10                  15

Pro Leu Gln Cys Ser Ala Leu Leu Val
            20                  25

<210> SEQ ID NO 3
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Lys Met Phe Pro Glu Val Lys Glu Lys Gly Met Ala Ala Leu Pro Arg
1               5                   10                  15

Leu Ile Ala Phe Thr Ser Glu His Ser His Phe Ser Leu Lys Lys Gly
                20                  25                  30

Ala Ala Ala Leu Gly Ile Gly Thr Asp Ser Val Ile Leu Ile Lys Cys
            35                  40                  45

Asp Glu Arg Gly Lys Met Ile Pro Ser Asp Leu Glu Arg Arg Ile Leu
        50                  55                  60

Glu Ala Lys Gln Lys Gly Phe Val Pro Phe Leu Val Ser Ala Thr Ala
65                  70                  75                  80

Gly Thr Thr

<210> SEQ ID NO 4
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Ile Ser Asn Met Tyr Ala Met Met Ile Ala Arg Phe Lys Met Phe
1               5                   10                  15

Pro Glu Val Lys Glu Lys Gly Met Ala Ala Leu Pro Arg Leu Ile Ala
                20                  25                  30

Phe Thr Ser Glu His Ser His Phe Ser Leu Lys Lys Gly Ala Ala Ala
            35                  40                  45

Leu Gly Ile Gly
            50

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Lys Asn Arg Glu Gly Tyr Glu Met Val Phe Asp Gly Lys Pro
1               5                   10                  15

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 6

Phe Phe Arg Met Val Ile Ser Asn Pro Ala Ala Thr His Gln Asp Ile
1               5                   10                  15

Asp Phe Leu Ile Glu Glu Ile Glu Arg Leu Gly Gln Asp Leu
            20              25                  30
```